United States Patent [19]
Rathjen et al.

[11] Patent Number: 5,795,859
[45] Date of Patent: Aug. 18, 1998

[54] PEPTIDE WHICH ABROGATES TNF AND/OR LPS TOXICITY

[75] Inventors: Deborah A. Rathjen; Fred Widmer; Geoffrey W. Grigg; Philip O. Mack, all of Sydney, Australia

[73] Assignee: Peptide Technology Limited, Dee Why, Australia

[21] Appl. No.: 178,268

[22] PCT Filed: Jul. 3, 1992

[86] PCT No.: PCT/AU92/00332

§ 371 Date: Mar. 15, 1994

§ 102(e) Date: Mar. 15, 1994

[87] PCT Pub. No.: WO93/01211

PCT Pub. Date: Jan. 21, 1993

[30] Foreign Application Priority Data

Jul. 5, 1991 [AU] Australia ................................ PK7097
Aug. 22, 1991 [AU] Australia ................................ PK7924

[51] Int. Cl.$^6$ ............................ A61K 38/00; C07K 14/00
[52] U.S. Cl. ........................ 514/12; 530/324; 530/387.12; 424/185.1
[58] Field of Search ........................ 530/387.2, 324; 514/12; 424/185.1

[56] References Cited

U.S. PATENT DOCUMENTS

| 4,508,728 | 4/1985 | Nagai et al. |
|---|---|---|
| 4,717,716 | 1/1988 | Nagai et al. |
| 5,118,500 | 6/1992 | Hanel et al. |
| 5,436,154 | 7/1995 | Barbanti et al. |

FOREIGN PATENT DOCUMENTS

| 0 303 380 | 8/1988 | European Pat. Off. |
|---|---|---|
| 0 341 100 | 11/1989 | European Pat. Off. |
| 0 313 654 | 7/1987 | United Kingdom |
| WO 90/06102 | 9/1989 | WIPO |
| WO 90/06938 | 6/1990 | WIPO |
| WO 90/06939 | 6/1990 | WIPO |
| WO 91/02078 | 2/1991 | WIPO |
| WO 91/02540 | 3/1991 | WIPO |
| WO 94/00555 | 1/1994 | WIPO |

OTHER PUBLICATIONS

**S.H. Socher et al. "Antibodies against amino acids 1.15 . . ." Proceedings of the National Academy of Sciences of the USA, vol. 84 No. 24 Dec. 1987, pp. 8755–9308.
Merck Manual, Fifteenth Edition, Merck & Co., Rahway, NJ (1987), see p. 1120.

*Primary Examiner*—Paula K. Hutzell
*Assistant Examiner*—Benet Prickril
*Attorney, Agent, or Firm*—Nixon & Vanderhye P.C.

[57] ABSTRACT

The present invention provides peptides which have the ability to abrogate TNF toxicity and/or LPS toxicity. The present invention further relates to compositions including these peptides as the active ingredient and methods of anti-inflammatory treatment involving the administration of this composition. The peptides of the present invention are based primarily on residue 1 to 26 of human TNF.

6 Claims, 22 Drawing Sheets

FIG. 1

VRSS SRTPSD 10 KPVAHVV ANP 20 QAEGQ LQWLN 30 RRA

NALLANG 40 VELRDNQ LVV 50 PSEGLYLIYS 60 QVLFKGQGCP 70 STHVLL

THTI 80 SRIAV SYQTK 90 VNLLSAIKSP 100 CQRETREGAE 110 AKPWYEPI

YL 120 GGVFQLEKGD 130 RLSAEINRPD 140 YLDFAESGQ V 150 YFGIIAL 157

PEPTIDE WHICH ABROGATES TNF AND/OR LPS TOXICITY

FIELD OF THE INVENTION

The present invention relates to a group of peptides which have the ability to abrogate TNF toxicity and/or LPS toxicity. The present invention further relates to compositions including this peptide as the active ingredient and methods of anti-inflammatory treatment involving the administration of this composition.

BACKGROUND OF THE INVENTION

Many of the clinical features of septicemic shock induced by Gram-negative bacteria which have lipopolysaccharide (LPS) in their cell walls may be reproduced in animals by the administration of LPS. This induces prompt severe metabolic and physiological changes which can lead to death. Associated with the injection of LPS is the extensive production of tumour necrosis factor alpha (TN ). Many of the effects of LPS injection or indeed of Gram-negative bacteria can be reproduced by TNE. Thus, mice injected with recombinant human TNF develop piloerection of the hair (ruffling), diarrhoea, a withdrawn, unkempt appearance and die if sufficient amounts are given. Rats treated with TNF become hypotensive, tachypneic and die of sudden respiratory arrest (Tracey et al., 1986 Science 234, 470). Severe acidosis, marked haemoconcentration and biphasic changes in blood glucose concentration were also observed. Histopathology revealed severe leukostatsis in the lungs, haemorraghic necrosis in the adrenals, pancreas and other organs and tubular necrosis of the kidneys. All these changes were prevented if the animals were pretreated with a neutralizing monoclonal antibody against TNF.

The massive accumulation of neutrophils in the lungs of TNF-treated animals reflects the activation of neutrophils by TNF. TNF causes neutrophil degranulation, respiratory burst, enhanced antimicrobiocidal and anti-tumour activity (Klebanoff et al., 1986 J. Immunol. 136, 4220; Tsujimoto et al., 1986 Biochem Biophys Res Commun 137, 1094). Endothelial cells are also an important target for the expression of TNF toxicity. TNF diminishes the anticoagulant potential of the endothelium, inducing procoagulant activity and down regulation of the expression of thrombomodulin (Stern and Nawroth, 1986 J Exp Med 163, 740).

TNF, a product of activated macrophages produced in response to infection and malignancy, was first identified as a serum factor in LPS treated mice which caused the haemorraghic necrosis of transplantable tumours in murine models and was cytoxoic for tumour cells in culture (Carswell et al., 1975 PNAS 72, 3666; Helson et al., 1975 Nature 258, 731). Cachexia is a common symptom of advanced malignancy and severe infection. It is characterised by abnormal lipid metabolism with hypertriglyceridemia, abnormal protein and glucose metabolism and body wasting. Chronic administration of TNF (also known as cachectin in the early literature) to mice causes anorexia, weight loss and depletion of body lipid and protein within 7 to 10 days (Cerami et al., 1985 Iununol Lett 11, 173, Fong et al., 1989 J Exp Med 170, 1627). These effects were reduced by concurrent administration of antibodies against TNF. Although TNF has been measured in the serum of patients with cancer and chronic disease associated with cachexia the results are inconclusive since large differences in TNF levels have been reported. These may be due to the short half-life of TNF (6 minutes), differences in TNF serum binding protein, or true differences in TNF levels in chronic disease states.

TNFα, as a mediator of inflammation, has been implicated in the pathology of other diseases apart from toxic shock and cancer-related cachexia. TNF has been measured in synovial fluid in patients with both rheumatoid and reactive arthritis and in the serum of patients with rheumatoid arthritis (Saxne et al., 1988 Arthrit. Rheumat. 31, 1041). Raised levels of TNF have been detected in renal transplant patients during acute rejection episodes (Maury and Teppo 1987 J. Exp Med 166, 1132). In animals TNF has been shown to be involved in the pathogenesis of graft versus host disease in skin and gut following allogeneic marrow transplantation. 10 Administration of a rabbit anti-marine TNF was demonstrated to prevent the histological changes associated with graft versus host disease and reduced mortality (Piauet et al., 1987 J Exp Med 166, 1280).

TNF has also been shown to contribute significantly to the pathology of malaria (Clark et al., 1987; Am. J. Pathol. 129: 192–199). Further, elevated serum levels of TNF have been reported in malaria patients (Scuderi et al., 1986; Lancet 2: 1364–1365). TNF may also contribute to the brain pathology and consequent dementia observed in late stage HIV infections (Grimaldi et al Ann Nevrol 29:21)

The peptides encompassed in the present invention do not necessarily interfere directly with the bio-synthetic mechanisms of the disease-causing component. As will be described below in the experimental data the mechanism behind the alleviating effect of the peptides is to be found in the modulation of the different cytokines produced by activated cells belonging to the cell-lines encompassing the immune defence. This modulation of cytokines is not limited to TNF but may also be valid for the whole range of interleukins, from interleukin-1 to interleukin 10. LPS a known component of bacteria important in inducing major inflammatory response was used as a model. LPS binds to receptors on neutrophils, monocytes, endothelial cells and machrophages which consequently become activated and start production of IL-1 and TNF and other cytokines, thus starting the inflammatory cascade. One parameter used to measure the effect of LPS is the concentration of blood glucose, which will normally decrease on exposure to TNF or LPS.

LPS normally combines with LPS-Binding-Protein (LBP) and exerts its dramatic effect through the CD14 receptor. The activation of the CD14 molecule by LPS results in TNF production by leucocytes. It is believed that the 10 peptides of the present invention which abrogate LPS toxicity may exert their effect by interacting with the CD14 molecule and thus inhibit LPS binding.

The peptides identified by the present inventors which have the ability to abrogate TNF and/or LPS toxicity resemble peptide sequences found in the amino terminal of TNFα. Other investigators have also considered this area of the TNFα molecule but with little success in obtaining biologically active peptides.

In this regard attention is drawn to Canadian patent application Nos 2005052 and 2005056 in the name of BASF AG. Both these applications claim a wide range of peptide sequences and, by selecting appropriate alternatives it can be seen that application No 2005052 is directed toward the peptide sequence 7–42 of TNFα whilst application No 2005056 is directed toward amino acid sequence 1 to 24 of TNFα. Whilst each of these applications claim a broad range of peptide sequences it is noted that there is no indication as to what, if any, biological activity the claimed peptides may possess. Indeed there is no demonstration that any of the produced peptide have any biological activity. In contrast, the present inventors have produced a range of peptides which have specific activities in that they abrogate TNF and/or LPS toxicity.

SUMMARY OF THE INVENTION

In a first aspect the present invention consists in a linear or cyclic peptide of the general formula:

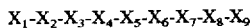

in which $X_1$ is null, Cys Or $R_1$ $X_2$ is null, Cys, $R_1$ or $A_1$-$A_2$-$A_3$-$A_4$-$A_5$ in which $A_1$ is Val or Ile or Leu or Met or His
$A_2$ is Arg or Cys or His
$A_3$ is Ser or Thr or Ala
$A_4$ is Ser or Thr or Ala
$A_5$ is Ser or Thr or Ala $X_3$ is Cys, $R_1$ or $A_6$-$A_7$ in which $A_6$ is Arg or Cys or His or Absent
$A_7$ is Thr or Ser or Ala $_4$ is Cys, $R_1$ or $A_8$–$A_9$ in which $A_8$ is Pro or an Nα-alkylamino acid
is $A_9$ is Ser or Thr or Ala $X_5$ is Cys, $R_1$ or $A_{10}$ in which $A_{10}$ is Asp or Ala or Cys or Glu or Gly or Arg or His $X_6$ is Cys, $R_2$ or $A_{11}$-$A_{12}$-$A_{13}$ in which $A_{11}$ is absent or Cys or Arg or His or Asp or Glu
$A_{12}$ is Pro or an Nα-alkylamino acid
$A_{13}$ is Val or Ile or Phe or Tyr or Trp or His or Leu or His or Met $X_7$ is null, Cys, $R_2$ or $A_{14}$-$A_{15}$ in which $A_{14}$ is Ala or Val or Gly or Ile or Phe or Trp or Tyr or Leu or His or Met
$A_{15}$ is absent or His or Arg or Glu or Asa or Ala or Lys or Asp or Phe or Tyr or Trp or Glu or Gln or Ser or Thr or Cly $X_8$ is null, Cys, $R_{21}$ $A_{16}$, $A_{16}$-$A_{17}$, $A_{16}$-$A_{17}$-$A_{18}$ or $A_{16}$-$A_{17}$-$A_{18}$-$A_{19}$-$A_{20}$-$A_{21}$-$A_{22}$-$A_{23}$-$A_{24}$-$A_{25}$-$A_{26}$ in which $A_{16}$ is Val or Ile or Leu or Met or His
$A_{17}$ is Val or Ile or Leu or Met or His
$A_{18}$ is Ala or Gly
$A_{19}$ is Asp or Glu
$A_{20}$ is Pro or an Nα-alkylamino acid
$A_{21}$ is Gln or Asn
$A_{22}$ is Ala or Gly
$A_{23}$ is Glu or Asp
$A_{24}$ is Gly or Ala
$A_{25}$ is Gln or Asn
$A_{26}$ is Leu or Ile or Val or Met or His $X_9$ is null, Cys or $R_2$ $R_1$ is R-CO, where R is X, straight, branched or cyclic alkyl up to C20, optionally containing double bonds and/or substituted with halogen, nitro, amino, hydroxy, sulfo, phospho or carboxyl groups (which may be substituted themselves), or aralkyl or aryl optionally substituted as listed for the alkyl and further including alkyl, or $R_1$ is glycosyl, nucleosyl, lipoyl or $R_1$ is an L- or D-α amino acid or an oligomer thereof consisting of up to 5 residues $R_1$ is absent when the amino acid adjacent is a desamino-derivative.

$R_2$ is
—$NR_{12}R_{13}$, wherein $R_{12}$ and $R13$ are independently H, straight, branched or cyclic alkyl, aralkyl or aryl optionally substituted as defined for $R_1$ or N-glycosyl or N-lipoyl
—$OR_{14}$, where $R_{14}$ is H, straight, branched or cyclic alkyl, aralkyl or aryl, optionally substituted as defined for $R_1$ —O-glycosyl, —O-lipoyl or
an L— or D-α-amino acid or an oligomer thereof consisting of up to 5 residues
or $R_2$ is absent, when the adjacent amino acid is a decarboxy derivative of cysteine or a homologue thereof or the peptide is in a N-C cyclic form, with the proviso that:

when $X_6$ is Cys or $R_2$ then $X_5$ is $A_{10}$, $X_4$ is $A_8$-$A_9$, $X_3$ is $A_6$-$A_7$ and $X_2$ is $A_1$-$A_2$-$A_3$-$A_4$-$A_5$ when $X_5$ is Cys or $R_1$ then $X_6$ is $A_{11}$-$A_{12}$-$A_{13}$, $X_7$ is $A_{14}$-$A_{15}$, $X_8$ is $A_{16}$-$A_{17}$-$A_{18}$ and $A_{11}$ is absent when $X_4$ is Cys or $R_1$ then $X_5$ is $A_{10}$, $X_6$ is $A_{11}$-$A_{12}$-$A_{13}$, $X_7$ is $A_{14}$-$A_{15}$ and is $A_{16}$-$A_{17}$-$A_{18}$ when $X_2$ is $A_1$-$A_2$-$A_3$-$A_4$-$A_5$ then $X_8$ is not $A_{16}$ when $X_1$ is null, $X_2$ is Cys or $R_1$, $X_3$ is $A_6$-$A_7$, $X_4$ is $A_8$-$A_9$, $X_5$ is $A_{10}$, $X_6$ is $A_{11}$-$A_{12}$-$A_{13}$, $X_7$ is $A_{14}$-$A_{15}$ and $X_8$ is $A_{16}$ then $A_{16}$ is not D-His.

$X_1$ is always and only null when $X_2$ is $R_1$, Lys or Null
$X_2$ is always and only null when $X_3$ is Cys or $R_1$
$X_3$ is always and only null when $X_6$ is Cys or $R_2$
$X_7$ is always and only null when $X_7$ is Cys, $R_2$ or Null
$X_8$ is always and only null when $X_8$ is Cys, $R_2$ or Null
$X_9$ is always and only null when $X_8$ is Cys, $R_2$ or Null when $X_1$ and $R_2$ are null, $X_3$ is $R_1$, $X_4$ is $A_8$-$A_9$, $X_5$ is $A_{10}$, $X_6$ is $A_{11}$-$A_{12}$-$A_{13}$, $X_7$ is $A_{14}$-$A_{15}$, $X_8$ is $R_2$ and $A_{14}$ is Ala and $A_{15}$ is absent then $R_1$ is acetyl and $R_2$ is $NH_2$.

The amino acids may be D or L isomers, however generally the peptide will primarily consist of L-amino acids.

In a second aspect the present invention consists in a pharmaceutical composition for use in treating subjects suffering from toxic effects of TNF and/or LPS, the composition comprising a therapeutically effective amount of a peptide of the first aspect of the present invention and a pharmaceutically acceptable sterile carrier.

In a third aspect the present invention consists in a method of treating a subject suffering from the toxic effects of TNF and/or LPS, the method comprising administering to the subject a therapeutically effective amount of the composition of the second aspect of the present invention.

In a preferred embodiment of the present invention
$X_1$ is H, $X_2$ is $A_1$-$A_2$-$A_3$-$A_4$-$A_5$, $X_3$ is $A_6$-$A_7$, $X_4$ is $A_8$-$A_9$, $X_5$ is $A_{10}$, $X_6$ is $A_{11}$-$A_{12}$-$A_{13}$, $X_7$ is $A_{14}$-$A_{15}$, $X_8$ is $A_{16}$-$A_{17}$-$A_{18}$ and $X_9$ is OH.

In a further preferred embodiment of the present invention
$X_1$ is null, $X_2$ is H or Ac, $X_1$ is $A_6$-$A_7$, $X_4$ is $A_8$-$A_9$, $X_5$ is $A_{10}$, $X_6$ is $A_{11}$-$A_{12}$-$A_{13}$, $X_7$ is $A_{14}$-$A_{15}$, $X_8$ is $A_{16}$-$A_{17}$-$A_{18}$ and $X_9$ is OH or $NH_2$.

In a further preferred embodiment of the present invention
$X_1$ is H, $X_2$ is $A_1$-$A_2$-$A_3$-$A_4$-$A_5$, $X_3$ is $A_6$-$A_7$, $X_4$ is $A_8$-$A_9$, $X_5$ is $A_{10}$, $X_6$ is OH and $X_6$, $X_7$ and $X_8$ are null.

In a further preferred embodiment of the present invention the peptide is selected from the group consisting of:

Val-Arg-Ser-Ser-Ser-Arg-Thr-Pro-Ser-Asp-Lys-Pro-Val-Ala-His-Val-Val-Ala;

Arg-Thr-Pro-Ser-Asp-Lys-Pro-Val-Ala-His-Val-Val-Ala;

Arg-Thr-Pro-Ser-Ala-Lys-Pro-Val-Ala-His-Val-Val-Ala;

Arg-Thr-Pro-Ser-Lys-Asp-Pro-Val-Ala-His-Val-Val-Ala;

Val-Arg-Ser-Ser-Ser- Arg-Thr-Pro-Ser-Asp-Lys-Pro-Val-Ala-Arg-Val-Val-Ala;

Val-Arg-Ser-Ser-Ser Arg-Thr-Pro-Ser-Asp-Lys-Pro-Val-Ala-Gln-VAL-Val-Ala;

Ac-Arg-Thr-Pro-Ser-Asp-Lys-Pro-Val-Ala-His-Val-NH$_2$;

Arg-Thr-pro-Ser-Asp-Lys -Pro-Val-Ala-Ala-Val;

Arg-Thr-Pro-Ser-Asp-Lys-Pro-Val-Ala-Lys-Val;

Arg-Thr-Pro-Ser-Asp-Lys-Pro-Val-Ala-His-Val-Val;

Pro-Ser-Asp-Lys-Pro-Val-Ala-His-Val;

Pro-Ser-Asp-Lys-Pro-Val-Ala-His;

Pro-Ser-Asp-Lys-Pro-Val;

Val-Arg-Ser-Ser-Ser-Arg-Thr-Pro-Ser-Asp-Lys-Pro-Val-Val-His-Val-Val-Ala;

Arg-Thr-Pro-Ser-Asp-Lys-Pro-Val-Ala-His-Val-Val-Ala-Asn-Pro-Gln-Ala-Glu-Gly-Gln-Leu;

Val-Arg-Ser-Ser-Ser-Arg-Thr-Pro-Ser-Asp;

Ac-Pro-Ser-Asp-Lys-Pro-Val-Ala-NH2;

Arg-Thr-Pro-Ser-Asp-Lys-Pro-Val-Ala-Asp-Val;

Val-Arg-Ser-Ser-Ser-Arg-Thr-Pro-Ser-Asp-Lys-Pro-Val-Ala-His-Val-Val-Ala-Asn-Pro-Gln-Ala-Glu-Gly-Gln-Leu;

Asp-Lys-Pro-Val-Ala-H is-Val-Val-Ala;

Arg-Thr-Pro-Ser-Asp-Lys-Pro-Val-Ala-His-Val;

Thr-Pro-Ser-Asp-Lys-Pro-Val-Ala-His-Val-Val-Ala;

Pro-Sir-Asp-Lys-Pro-Val-Ala-His-Val-Val-Ala;

Pro-Val-Ala-His-Val-Val-Ala; and

Arg-Thr-Pro-Ser-Asp-Lys-Pro-Val-Val-His-Val.

The composition and method of the present invention would be expected to be useful as an anti-inflammatory agent in a wide range of disease states including toxic shock, adult respiratory distress syndrome, hypersensitivity pneumonitis, systemic lupus erythromatosis, cystic fibrosis, asthma, bronchitis, drug withdrawal, schistosomiasis, sepsis, rheumatoid arthritis, acquired immuno-deficiency syndrome, multiple sclerosis, leperosy, malaria, systemic vasculitis, bacterial meningitis, cachexia, dermatitis, psoriasis, diabetes, neuropathy associated with infection or autoimmnne disease, ischemia/reperfusion injury, encephalitis, Guillame Barre Syndrome, atherosclerosis, chronic fatigue syndrome, TB, other viral and parasitic diseases, OKT3 therapy, and would be expected to be useful in conjunction with radiation therapy, chemotherapy and transplantation, to ameliorate the toxic effects of such treatments or procedures.

As the peptide of the present invention suppresses activation of neutrophils the composition and method of the present invention may also be useful in the treatment of diseases with an underlying element of local, systemic, acute or chronic inflammation. In general, it is believed the composition and method of the present invention will be useful in treatment of any systemic or local infection leading to inflammation.

The peptides of the present invention may also be administered in cancer therapy in conjunction with cytotoxic drugs which may potentiate the toxic effects of TNFα (Watanabe et al., 1988; immunopharmacol. Immunotoxicol. 10: 117–127) such as vinblastin, acyclovir, interferon alpha, cyclosporin A, IL-2, actinomycin D, adriamycin, mitomycin C, AZT, cytosine arabinoside, daunororubin, cis-platin, vincristine, 5-flurouracil and bleomycin; in cancer patients undergoing radiation therapy; and in AIDS patients (or others suffering from viral infection such as viral meningitis, hepatitis, herpes, green monkey virus etc.) and in patients receiving immunostimulants such as thymopentin and muramyl peptides or cytokines such as IL-2 and C-M-CSF. In this use peptides of the present invention will serve to abrogate the deleterious effects of TNFα.

It will be appreciated by those skilled in the art that a number of modifications may be made to the peptide of the present invention without deleteriously effecting the biological activity of the peptide. This may be achieved by various changes, such as insertions, deletions and substitutions (e.g., sulfation, phosphorylation, nitration, halogenation), either conservative or non-conservative (e.g., W-amino acids, desamino acids) in the peptide sequence where such changes do not substantially altering the overall biological activity of the peptide. By conservative substitutions the intended combinations are:- C, A; V, I, L, M; D, E; N, Q; S, T; K, R, H; F, Y, W, H; and P, Nα-alkylamino acids.

It may also be possible to add various groups to the peptide of the present invention to confer advantages such as increased potency or extended half-life in vivo, without substantially altering the overall biological a activity of the peptide.

The term peptide is to be understood to embrace peptide bond replacements and/or peptide mimetics, i.e. pseudopeptides as recognised in the art (see for example; Proceedings of the 20th European Peptide Symposium, edt. G. Jung. E. Bayer, pp. 289–336, and references therein), as well as salts and pharmaceutical preparations and/or formulations which render the bioactive peptide(s) particularly suitable for oral, topical, nasal spray, ocular pulmonary, I.V., subcutaneous, as the case may be, delivery. Such salts, formulations, amino acid replacements and pseudopeptide structures may be necessary and desirable to enhance the stability, formulation, deliverability (e.g., slow release, prodrugs), or to improve the economy of production, and they are acceptable, provided they do not negatively affect the required biological activity of the peptide.

Apart from substitutions, three particular forms of peptide mimetic and/or analogue structures of particular relevance when designating bioactive peptides, which have to bind to a receptor while risking the degradation by proteinases and peptidases in the blood, tissues and elsewhere, may be mentioned specifically, illustrated by the following examples: Firstly, the inversion of backbone chiral centres leading to D-amino acid residue structures may, particularly at the N-terminus, lead to enhanced stability for proteolytical degradation while not impairing activity. An example is given in the paper "Tritriated D-ala$^1$-Peptide T Binding", Smith, C. S. et al, Drug Development Res. 15, pp. 371–379 (1988). Secondly, cyclic structure for stability, such as N to C interchain imides and lactames (Ede et al in Smith and Rivier (Eds) "Peptides: Chemistry and Biology", Escom. Leiden (1991), p268–270), and sometimes also receptor binding may be enhanced by forming cyclic analogues. An example of this is given in "Confirmationally restricted thymopentin-like compounds", U.S. pat. No. 4,457,489 (1985), Goldstein., G. et al. Finally, the introduction of ketomethylene, methylsulfide or retroinverse bonds to replace peptide bonds, i.e. the interchange of the CO and NE moieties may both greatly enhance stability and potency. An example of the latter type is given in the paper "Biologically active retroinverso analogues of thymopentin", Sisto A. et al in Rivier, J. E. and Marshall, G. R. (eds.) "Peptides, Chemistry, Structure and Biology", Escom, Leiden (1990), p.722–773.

The peptides of the invention can be synthesized by various methods which are known in principle, namely by chemical coupling methods (cf. Wunsch, E.: "Methoden der organischen Chemie", Volume 15, Band 1+2, Synthese von Peptiden, Thieme Verlag, Stuttgart (1974), and Barrany, G.; Merrifield, R.B: "The Peptides", eds. E. Gross, J. Meienhofer., Volume 2, Chapter 1, pp. 1–284, Academic Press (1980)), or by enzymatic coupling methods (cf. Widmer, F., Johansen, J. T., Carlsberg Res. Commun., Volume 44, pp. 37–46 (1979), and Kullmann, W.: "Enzymatic Peptide Synthesis", CRC Press Inc., Boca Raton, Florida (1987), and Widmer, F., Johansen, J. T. in "Synthetic Peptides in Biology and Medicine:, eds., Alitalo, K., Partanen, P., Vatieri, A., pp. 79–86, Elsevier, Amsterdam (1985)), or by a combination of chemical and enzymatic methods if this is advantageous for the process design and economy.

It will be seen that one of the alternatives embraced in the general formula set out above is for a cysteine residue to be positioned at both the amino and carboxy terminals of the peptide. This will enable the cylisation of the peptide by the formation of di-sulphide bond.

It is intended that such modifications to the peptide of the present invention which do not result in a decrease in biological activity are within the scope of the present invention.

As would be recognized by those skilled in the art there are numerous examples to illustrate the ability of anti-idiotypic (anti-Ids) antibodies to an antigen to function like that antigen in its interaction with animal cells and components of cells. Thus, anti-ids to a peptide hormone antigen can have hormone-like activity and interact specifically with the receptors to the hormone. Conversely, anti-Ids to a receptor can interact specifically with a mediator in the same way as the receptor does. (For a review of these properties see: Gaulton, G. N. and Greane, M. I. 1986. Idiotypic mimicry of biological receptors, Ann. Rev. Immunol. A, 253–280; Sege, PC and Peterson, P. A., 1978. Use of anti-iodiotypic antibodies as cell surface receptor probes. Proc. Natl. Acad. Sci. U.S.A 75, 2443–2447).

As might be expected from this functional similarity of anti-Id and antigen, anti-Ids bearing the internal image of an antigen can induce immunity to such an antigen. (This nexus is reviewed in Hiernaux, J. R. 1988. Idiotypic vaccines and infectious diseases. Infect. Imnun. 56, 1407–1413.)

As will be appreciated by persons skilled in the art from the disclosure of this application it will be possible to produce anti-idiotypic antibodies to the peptide of the present invention which will have similar biological activity. It is intended that such anti-idiotypic antibodies are included within the scope of the present invention.

Accordingly, in a fourth aspect the present invention consists in an anti-idiotypic antibody to the peptide of the first aspect of the present invention, the anti-idiotypic antibody being capable of abrogating TNF and/or LPS toxicity.

The individual specificity of antibodies resides in the structures of the peptide loops making up the Complementary Determining Regions (CDRs) of the variable domains of the antibodies. Since in general, the amino acid sequences of the CDR peptide loops of an anti-Id are not identical to or even similar to the amino acid sequence of the peptide antigen from which it was originally derived, it follows that peptides whose amino acid sequence is quite dissimilar, in certain contexts can take up a very similar three-dimensional structure. The concept of this type of peptide, termed a "functionally equivalent sequence" or mimotope by Geyson is familiar to those expert in the field. (Geyson, H. M. et al 1987. Strategies for epitope analysis using peptide synthesis. J. Immun. Methods 102, 259–274).

Moreover, the three-dimensional structure and function of the biologically active peptides can be simulated by other compounds, some not even peptidic in nature, but which mimic the activity of such peptides. This field of science is summarised in a review by Goodman, M. (1990). (Synthesis, spectroscopy and computer simulations in peptide research. Proc. 11th American Peptide Symposium published in Peptides-Chemistry, Structure and Biology pp 3–29. Ed Rivier, J. E. and Marshall, G. R. Publisher ESCOM.)

As will be recognized by those skilled in the art, armed with the disclosure of this application, it will be possible to produce peptide and non-peptide compounds having the same three-dimensional structure as the peptide of the present invention. These "functionally equivalent structures" or "peptide mimics" will react with antibodies raised against the peptide of the present invention and may also be capable of abrogating TNF toxicity. It is intended that such "peptide mimics" are included within the scope of the present invention.

Accordingly, in a fifth aspect the present invention consists in a compound the three-dimensional structure of which is similar as a pharmacophore to the three-dimensional structure of the peptide of the first aspect of the present invention, the compound being characterized in that it reacts with antibodies raised against the peptide of the first aspect of the present invention and that the compound is capable of abrogating TNF and/or LPS toxicity.

More detail regarding pharmacophores can be found in Bolin et al. p 150, Polinsky et al. p 287, and Smith et al. p 485 in Smith and Rivier (Eds) "Peptides: Chemistry and Biology", Escom, Leiden (1991).

DETAIL DESCRIPTION OF THE INVENTION

In order that the nature of the present invention may be more clearly understood, the preferred forms thereof will now be described with reference to the following example and accompanying Figures and Tables in which:

FIG. 1 shows the amino acid sequence of human TNFα;

FIG. 2 Effect of TNF (◊) and TNF+ Peptide 1 (♦) on blood glucose levels in malaria primed mice-Peptide 1 abrogates Thy induced hypoglycaemia in malaria primed mice.

FIG. 3 Effect of Peptide 1 on TNF-induced tumour regression.

FIG. 4 Effect of Peptide 1 (●), peptide 308 (▼), peptide 309 (■), peptide 305 (◊) and peptide 302 (○) on binding of radiolabelled TNF to TNF receptors on WEH1-164 tumour cells— Peptide 1 does not inhibit binding of TNF to tumour cells.

FIG. 5 Plasma reactive nitrogen intermediate levels in TNF. Peptide 1 treated malaria primed mice— this shows that induction of RNI by TNF is inhibited by treatment with Peptide 1.

FIG. 6 shows the effect on blood glucose levels in mice treated with PBS (◊); TNF alone (♦); TNF+ Peptide 1 (■) and TNF+Peptide 2 (○)

PRODUCTION OF PEPTIDES

Synthesis of Peptides Using the FMOC-Strategy

Figure 2:
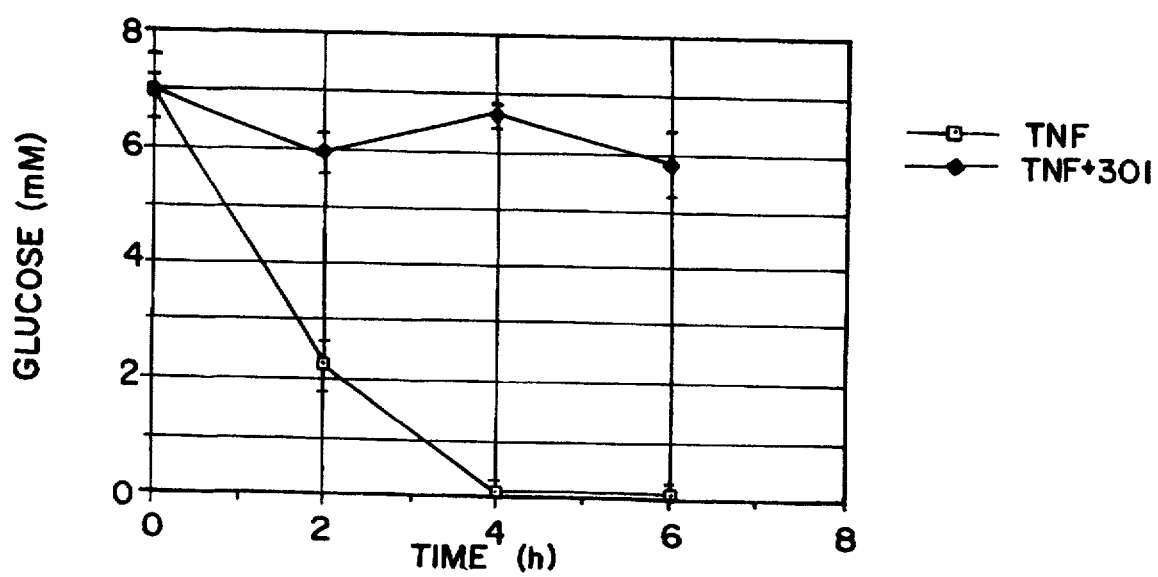

Peptides (1–6, 9–18, 22–25, 27–29, 35, 36, 39, 40 Table 3) were synthesized on the continuous flow system as provided by the Milligen synthesizer Model 9050 using the standard Fmoc-polyamide method of solid phase peptide synthesis (Atherton et al, 1978. J.Chem. Soc. Chem. Commun., 13, 537–539).

For peptides with free carboxyl at the C-terminus, the solid resin used was PepSyn KA which is a polydimethylacrylamide gel on Kieselguhr support with 4-hydroxymethylphenoxyacetic acid as the functionalised linker (Atherton et al., 1975, J.Am.Chem.Soc 97, 6584–6585). The carboxy terminal amino acid was attached to the solid support by a DCC/DMP-mediated symmetrical-anhydride esterification.

For peptides with carboxamides at the C-terminus, the solid resin used was Fmoc-PepSyn L Am which is analogous polyamides resin with a Rink linker, p-[(R.S)-α[1-(9H-fluoren-9-yl)-methoxyformamido]-2.4-dimethoxybenzyl]-phenoxyacetic acid (Bernatowicz et al. 1989, Tet.Lett. 30, 4645). The synthesis starts by removing the Fmoc-group with an initial piperidine wash and incorporation of the first amino acid is carried out by the usual peptide coupling procedure.

The Fmoc strategy was also carried out in the stirred cell system in synthesis of peptides (33,34,37,38) where the Wang resin replaced the Pepsyn KA.

All Fmoc-groups during synthesis were removed by 20% piperidine/DMF and peptide bonds were formed either of the following methods except as indicated in Table 1:

1. Pentafluorophenyl active esters. The starting materials are already in the active ester form.

2. Hydroxybenzotriazol esters. These are formed in situ either using Castro's reagent, BOP/NMM/HOBt (Fournier et al. 1989, Int. J. Peptide Protein Res., 33, 133–139) or using Knorr's reagent, HBTU/NMM/HOBt (Knorr et al. 1989, Tet. Lett., 30 , 1927).

Side chain protection chosen for the amino acids was removed concomitantly during cleavage with the exception of Acm on cysteine which was left on after synthesis. Intramnolecular disulphide bridges where needed are then formed by treating the Acm protected peptide with iodine/methanol at high dilution.

TABLE 1

| Amino Acid | Protecting Group | Coupling Method |
| --- | --- | --- |
| Arg | Pmc | HOBt or OPfp |
| Asp | OBut | HOBt or OPfp |
| Cys | Acm | HOBt or OPfp |
| Glu | OBut | HOBt or OPfp |
| His | Boc or Trt | HOBt or OPfp |
| Lys | But | HOBt or OPfp |
| Ser | But | HOBt only |
| Thr | But | HOBt only |
| Tyr | But | HOBt or OPfp |
| Asn | none | OPfp only |
| Gln | none | OPfp only |

Cleavage Conditions

Peptides were cleaved from the PepSyn KA and PepSyn K Am using 5% water and 95% TFA where Arg(Pmc) is not present. Where Arg(Pmc) is present a mixture of 5% thioanisole in TFA is used. The cleavage typically took 3 h at room temperature with stirring. Thioanisole was removed by washing with ether or ethyl acetate and the peptide was extracted into an aqueous fraction. Up to 30% acetonitrile was used in some cases to aid dissolution. Lyophilization of the aqueous/acetonitrile extract gave the crude peptide.

Peptides from the wang resin were cleaved using 5% phenol, 5% ethanedithiol and 90% TFA for 16 h at ambient temperature with stirring. Thioanisole was removed by washing with ether or ethyl acetate and the peptide was extracted into an aqueous fraction. Up to 30% acetonitrile was used in some cases to aid dissolution. Lyophilization of the aqueous/acetonitrile extract gave the crude peptide.

Peptides from the Wang resin were cleaved using 5% phenol, 5% ethanedithiol and 90% TFA for 16 h at ambient temperature with stirring.

Purification

Crude peptide is purified by reverse phase chromatography using either a C4 or C18 column and the Buffer system: Buffer A-0.1% aqueous TFA, Buffer B-80% Acetonitrile and 20% A.

N-Terminal Acetylation

The peptide resin obtained after the synthesis (with Fmoc removed in the usual manner was) placed in a 0.3 MDMF solution of 10 equivalents of Ac-OHSu for 60 minutes. The resin was filtered, washed with DMF, CH2C12, ether and used in the next step.

Cyclization

The purified and lyophilized bis-S-(acetamidomethyl) cysteine peptide (100–400 mg) was dissolved in 5 mls of methanol containing 1 ml of acetic acid. This was added dropwise to a 1 litre methanol solution containing 1 g of iodine.

After 2 h reaction, the excess iodine was removed by addition of a dilute sodium thiosulfate solution until the colour turns to a pale yellow, methanol was removed in vacuo at room temperature and the concentrated solution was finally completely decolourised with dropwise addition of sodium thiosulfate and applied immediately onto a preparatively reverse phase chromatography column.

Synthesis of Peptides using the Boc-Strategy

Syntheses of these peptides were carried out on the ABI 430A instrument using polystyrene based resins. For peptide with C-terminal acids, the appropriate Merrified resin Boc-amino acid-O-resin or the 100–200 mesh PAM resin is used (7, 8, 19–21, 26, 31). Peptides with C-terminal amides are synthesized on MBHA resins (32, 33).

Couplings of Boc-amino acids (Table 2) were carried out either using symmetrical anhydride method or a HOBt ester method mediated by DCC or HTBU.

TABLE 2

| Amino Acid | Protecting Group | Coupling Method |
| --- | --- | --- |
| Arg | Tos | HOBt or S.A. |
| Asp | Cxl, OBzl | HOBt or S.A. |
| Cys | 4-MeBzl | HOBt or S.A. |
| Glu | Cxl | HOBt or S.A. |
| His | Dnp, Bom | HOBt or S.A. |

TABLE 2-continued

| Amino Acid | Protecting Group | Coupling Method |
| --- | --- | --- |
| Lys | 2-Clz | HOBt or S.A. |
| Ser | Bzl | HOBt or S.A. |
| Thr | Bzl | HOBt or S.A. |
| Tyr | Bzl | HOBt or S.A. |
| Asn | Xan | HOBt or S.A. |
| Gln | none | HOBt only |

Cleavage

Peptides were cleaved in HF with p-cresol or anisole as scavenger for up to 90 min. For His with Dnp protection, the resin required pre-treatment with mercaptoethanol:DIPEA:DMF (2:1:7), for 30 min. After removal of scavengers by ether wash, the crude peptide is extracted into 30% acetonitrile in water.

N-Terminal Acetylation

Acetylation was achieved by treating the deblocked resin with acetic anhydride in DMF solution.

TABLE 3

| No | hTNF | Sequence |
| --- | --- | --- |
| 1 | 1–18 | VAL ARG SER SER SER ARG THR PRO SER ASP LYS PRO VAL ALA HIS VAL VAL ALA (SEQ ID NO: 1) |
| 2 | 6–18 | ARG THR PRO SER ASP LYS VAL PRO ALA HIS VAL VAL ALA (SEQ ID NO: 2) |
| 3 | 2–15 | ART SER SER SER ARG THR PRO SER ASP LYS PRO VAL ALA HIS (SEQ ID NO: 3) |
| 4 | 1–26 | VAL ARG SER SER SER ARG THR PRO SER ASP LYS PRO VAL ALA HIS VAL VAL ALA ASN PRO GLN ALA GLU GLY GLN LEU (SEQ ID NO: 4) |
| 5 | 10–18 | ASP LYS PRO VAL ALA HIS VAL VAL ALA (SEQ ID NO: 5) |
| 6 | 15–22 | HIS VAL VAL ALA ASN PRO GLN ALA (SEQ ID NO: 6) |
| 7 | 6–16 | ARG THR PRO SER ASP LYS PRO VAL ALA HIS VAL (SEQ ID NO: 7) |
| 8 | 6–17 | ARG THR PRO SER ASP LYS PRO VAL ALA HIS VAL VAL (SEQ ID NO: 8) |
| 9 | 8–16 | PRO SER ASP LYS PRO VAL ALA HIS VAL (SEQ ID NO: 9) |
| 10 | 8–15 | PRO SER ASP LYS PRO VAL ALA HIS (SEQ ID NO: 10) |
| 11 | 8–15 | PRO SER ASP LYS PRO VAL ALA (SEQ ID NO: 11) |
| 12 | 8–13 | PRO SER ASP LYS PRO VAL (SEQ ID NO: 12) |
| 13 | 7–18 | THR PRO SER ASP LYS PRO VAL ALA HIS VAL VAL ALA (SEQ ID NO: 13) |
| 14 | 8–18 | PRO SER ASP LYS PRO VAL ALA HIS VAL VAL ALA (SEQ ID NO: 14) |
| 15 | 9–18 | SER ASP LYS PRO VAL ALA HIS VAL VAL ALA (SEQ ID NO: 15) |
| 16 | 11–18 | LYS PRO VAL ALA HIS VAL VAL ALA (SEQ ID NO: 16) |
| 17 | 12–18 | PRO VAL ALA HIS VAL VAL ALA (SEQ ID NO: 17) |
| 18 | 12–18 | Ac PRO VAL ALA HIS VAL VAL ALA NH2 (SEQ ID NO: 18) |
| 19 | 6–18 Ala(10) | ARG THR PRO SER ALA LYS PRO VAL ALA HIS VAL VAL ALA (SEQ ID NO: 19) |
| 20 | 6–18 Ala(11) | ARG THR PRO SER ASP ALA PRO VAL ALA HIS VAL VAL ALA (SEQ ID NO: 20) |
| 21 | 6–18 | ARG THR PRO SER LYS ASP PRO VAL ALA HIS VAL VAL ALA (SEQ ID NO: 21) |
| 22 | Lys(10) Asp(11) 1–18 | VAL ARG SER SER SER ARG THR PRO SER ASP LYS PRO VAL ALA ARG VAL VAL ALA (SEQ ID NO: 22) |
| 23 | Arg(15) 1–18 GLN(15) | VAL ARG SER SER SER ARG THR PRO SER ASP LYS PRO VAL ALA GLN VAL VAL ALA (SEQ ID NO: 23) |
| 24 | 1–18 Leu(14) | VAL ARG SER SER SER ARG THR PRO SER ASP LYS PRO VAL LEU HIS VAL VAL ALA (SEQ ID NO: 24) |
| 25 | 1–18 | VAL ARG SER SER SER ARG THR PRO SER ASP |

TABLE 3-continued

| No | hTNF | Sequence |
|---|---|---|
| | | LYS PRO VAL <u>VAL</u> HIS VAL VAL ALA (SEQ ID NO: 25) |
| | Val(14) | |
| 26 | 6–26 | ARG THR PRO SER ASP LYS PRO VAL ALA HIS VAL VAL ALA ASN PRO GLN ALA GLU GLY GLN LEU (SEQ ID NO: 26) |
| 27 | 1–16 | VAL ARG SER SER SER ARG THR PRO SER ASP LYS PRO VAL ALA HIS VAL (SEQ ID NO: 27) |
| 28 | 1–10 | VAL ARG SER SER SER ARG THR PRO SER ASP (SEQ ID NO: 28) |
| 29 | 8–14 | Ac PRO SER ASP LYS PRO VAL ALA NH2 (SEQ ID NO: 29) |
| 30 | 6–16 | Ac ARG THR PRO SER ASP LYS PRO VAL ALA HIS VAL NH2 (SEQ ID NO: 30) |
| 31 | 6–16 | ARG THR PRO SER ASP LYS PRO VAL <u>VAL</u> HIS VAL (SEQ ID NO: 31) |
| | Val(14) | |
| 32 | 6–16 | ARG THR PRO SER ASP LYS PRO VAL ALA HIS ALA (SEQ ID NO: 32) |
| | ALA(16) | |
| 33 | 6–16 | ARG THR PRO SER ASP LYS PRO VAL ALA <u>ALA</u> VAL (SEQ ID NO: 33) |
| | ALA(15) | |
| 34 | 6–16 | ARG THR PRO SER ASP LYS PRO VAL ALA <u>LYS</u> VAL (SEQ ID NO: 34) |
| | LYS(15) | |
| 35 | 6–16 | ARG THR PRO SER ASP LYS PRO VAL ALA <u>ASP</u> VAL (SEQ ID NO: 35) |
| | ASP(15) | |
| 36 | 6–16 | ARG THR PRO SER ASP LYS PRO VAL ALA HIS VAL (SEQ ID NO: 36) |
| | D-HIS(15) | |
| 275 | 111–120 | ALA LYS PRO TRP TYR GLU PRO ILE TYR LEU (SEQ ID NO: 37) |
| 302 | 43–48 | LEU ARG ASP ASN GLN LEU VAL VAL PRO SER GLU GLY LEU TYR LEU ILE (SEQ ID NO: 38) |
| 303 | 94–109 | LEU SER ALA ILE LYS SER PRO LYS GLN ARG GLU THR PRO GLU GLY ALA (SEQ ID NO: 39) |
| 304 | 63–83 | LEU PHE LYS GLY GLN GLY CYS PRO SER THR HIS VAL LEU LEU THR HIS THR ILE SER ARG ILE (SEQ ID NO: 40) |
| 305 | 132–150 | LEU SER ALA GLU ILE ASN ARG PRO ASP TYR LEU ASP PHE ALA GLU SER GLY GLN VAL (SEQ ID NO: 41) |
| 306 | 13–26 | VAL ALA HIS VAL VAL ALA ASN PRO GLN ALA GLU GLY GLN LEU (SEQ ID NO: 42) |
| 307 | 22–40 | ALA GLU GLY GLN LEU GLN TRP LEU ASN ARG ARG ALA ASN ALA LEU LEU ALA ASN GLY (SEQ ID NO: 43) |
| 308 | 54–68 | GLY LEU TYR LEU ILE TYR SER GLN VAL LEU PHE LYS GLY GLN GLY (SEQ ID NO: 44) |
| 309 | 73–94 | HIS VAL LEU LEU THR HIS THR ILE SER ARG ILE ALA VAL SER TYR GLN THR LYS VAL ASN LEU LEU (SEQ ID NO: 45) |
| 323 | 79–89 | THR ILE SER ARG ILE ALA VAL SER TYR GLN THR (SEQ ID NO: 46) |
| 347 | 132–157 | LEU SER ALA GLU ILE ASN ARG PRO ASP TYR LEU ASP PHE ALA GLU SER GLY GLN VAL TYR PHE GLY ILE ILE ALA LEU (SEQ ID NO: 47) |

Endothelial Cell Clotting Assays

Endothelial cell procoagulant activity (PCA) induction by TNFα was determined using bovine aortic endothelial cells (BAE) according to the procedure of Bevilacqua et al., 1986 PNAS 83, 4522 with the following modifications: BAE cells were propagated in McCoys 5A medium supplemented with 10% FCS, penicillin, streptomycin and L-gutamine in standard tissue culture flasks and 24-well dishes. TNFα treatment of culture (3 μg/ml) was for 4 hours at 37° C. in the presence of growth medium after which the cells were washed and scrape-harvested before being frozen, thawed and sonicated. Total cellular PCA was determined in a standard one-stage clotting assay using normal donor platelet poor plasma to which 100 μl of CaCl$_2$ and 100 μl of cell lystate was added. Statistical significance was determined by unpaired t-test.

Neutrophil Activation Studies

In these experiments, neutrophils were prepared from blood of healthy volunteers by the rapid single step method (Kowanko and Ferrante 1987 Immunol 62, 149). To 100 μl of 5×10$^6$ neutrophils/ml was added 100 μl of either 0, 10, 100 μg of peptide/ml and 800 μl of lucigenin (100 μg). The tubes were immediately placed into a light proof chamber (with a 37° C. water jacket incubator) of a luminometer (model 1250; LKB Instruments, Wallac, Turku, Finaldn). The resultant light output (in millivolts was recorded). The results are recorded as the maximal rate of chemiluminescence production.

Effects of Peptides on neutrophil chemiluminescence induced by either TNF or LPS: Neutrophils of 96–99% purity and >99% viability were prepared from blood of normal healthy volunteers by centrifugation (400 g for 30 min) through Hypaque-Ficoll medium of density 1.114. Following centrifugation the neutrophils formed a single band above the erythrocytes and 1 cm below the mononuclear leukocyte band. These were carefully recovered and washed in medium 199. To assess the lucigenin-dependent chemiluminescence response 100 μl of 5×10⁶ neutrophils/ml was added 100 μl of either 0.1.10.100 μg of peptide/ml and TNF or LPS and 800 μl of lucigenin (100 μg). The tubes were immediately placed into a light proof chamber with a 37° C. water jacket incubator of a luminometer. The resultant light output (in millivolts) was recorded. The results are recorded as the maximal of chemiluminescence production. In experiments which examined the ability of the peptides to prime for the response to fMLP. 100 μl of 5×10⁵ neutrophils/ml preincubated in peptide and LPS or TNF for 20 mins was added to 100ul of diluent or fMLP (5×10⁶M) before the addition of 700 μl of lucigenin (100 μg). The chemiluminescence was measured as above. Neutrophils from at least three individuals were used in triplicate determinations of anti-TNF or LPS activity. Results were deemed positive if at least 50% inhibition of chemiluminescence was obtained in at least two thirds of cases.

WEH1-164 Cytoxicty

Bioassay of recombinant TNF activity was performed according to the method described by Espevik and Nisssen-Meyer. (Espevik and Nissen-Meyer 1986 J. Immuunol. Methods 99–105)

Tumour Regression Experiments

Subcutaneous tumours were induced by the injection of approximately 5×10⁵ WEH1-164 cells. This produced tumours of diameters of 10 to 15 mm approximately 14 days later. Mice were injected i.p. with recombinant human TNF (10 μg and 20 μg) and peptide (1 mg) for four consecutive days. Control groups received injections of PBS. Tumour size was measured daily throughout the course of the experiment. Statistical significance of the results was determined by unpaired Student T-test.

Radioreceptor assays

WEH1-164 cells grown to confluency were scrape harvested and washed once with 1% bovine serum albumin in Hanks balanced salt solution (HBSS, Gibco) and used at 2×10⁶ cells pre assay sample. For the radioreceptor assay, the cells were incubated with varying amounts of either unlabelled TNFα(1–10⁴ ng per assay sample) or peptide (0–10⁵ ng per assay sample) and ¹²⁵I-TNF (50.000 cpm) for 3 hours at 37° C. in a shaking water bath. At the completion of the incubation 1 ml of HBSS/BSA was added to the WEH1-164 cells, the cells spun and the bound ¹²⁵I in the cell pellet counted. Specific binding was calculated from total binding minus non-specific binding of triplicate assay tubes. 100% specific binding corresponded to 1500 cpm.

In Vivo Studies of TNF Toxicity

Mice were administered with either TNF (200 μg), Peptide 1 (10 mg) and TNF (200 μg)+Peptide 1 (10 mg) via intravenous injection. Blood glucose levels and appearance of the animals was evaluated at 15, 30, 60, 120, 180 minutes after injection. Appearance parameters which were evaluated included ruffling of fur, touch sensitivity, presence of eye exudate, light sensitivity and diarrhoea.

Infection of mice with malaria parasites and treatment with TNT+ Peptide 1

All the mice used were male. CBA/CaH stain and 6–8 weeks old. P. vinkei vinkei (Strain V52, from F.E.G. Cox, London) has undergone several serial passages in CBA mice, after storage in liquid nitrogen, before use in these experiments. Infections were initiated by intraperitoneal injection of 10⁶ parasitized erythrocytes. Mice were treated with TNF(7 μg) ± peptide (8.3 mg) administered iv.

Assays for blood glucose

Nonfasting blood glucose levels were determined on a Beckman Glucose Analyzer 2 (Beckman Instruments) or on a Exectech blood glucose sensor (Clifford Hallam Pty. Ltd).

Reactive Nitrogen Intermediates (RNI)

RNI levels in blood were determined by the method of Rockett et al (1991) in-vivo induction of TNF, LT and IL-1 implies a role for nitric oxide in cytokine-induced malarial cell-mediated immunity and pathology. J. Immunol. in press.

TNF And LPS Lethality Experiments: balb/C or balbC x swiss F1 mice carrying Meth A ascites tumours elicited by prior I.P. inoculation of 0.5 μl pristane 7 days before I.P. injection of tumour cells. Nine to ten days after inoculation with the tumour cells 25 μg of human recombinant TNF was subcutaneously administered and a short time later 1 mg of either test peptide, bovine serum albumen, phosphate buffered saline or neutralizing anti-TNF MAb 47 was administered at a separate subcutaneous site. The number of surviving animals was then observed at 18 hours and 24 hours post TN? treatment. In experiments which assessed the effects of 1-related peptides on on LPS lethality the mice were administered 500 μg E.coli LPS and peptide or other treatment in a similar manner. In LPS experiments polymyxin B, an LPS inhibitor, replaced MAb 47 as a positive control. The number of animals surviving was assessed at intervals up to 64 hours after LPS challenge.

Experiments in D-galactosamine sensitized mice: Female Bablb/C mice were co-injected intraperitoneally with 16 mg D-galactosamine and 2 μg human recombinant TNF. The mice were then injected subcutaneously with either test peptide, phosphate buffered saline or neutralizing anti-TN? monoclonal antibody 47. The number of surviving animals was assessed at intervals up to 48 hours after TNF challenge.

RESULTS

The results obtained with each of the peptides are summarised in Table 4. A single ★ indicates heightened activity in that test whilst a double ★★ indicates activity at low concentrations of peptide but not high concentrations.

TABLE 4

| | IN VIVO | | | IN VITRO NEUTROPHIL | | | |
|---|---|---|---|---|---|---|---|
| | TNF TOXICITY | | LPS TOXICITY | TNF | | LPS | |
| PEPTIDE | METH A | D-GAL | METH A | DIRECT | PRIMING | DIRECT | PRIMING |
| 1 | + | + | + | + | + | + | + |
| 2 | +* | + | + | +* | | | |
| 8 | − | | − | + | | | |
| 9 | − | | − | +** | | | |
| 10 | +* | − | − | + | | | |
| 11 | − | | | − | | | |
| 12 | + | | | − | | | |
| 16 | − | | | − | | | |

TABLE 4-continued

| | IN VIVO | | | IN VITRO NEUTROPHIL | | | |
|---|---|---|---|---|---|---|---|
| | TNF TOXICITY | | LPS TOXICITY | TNF | | LPS | |
| PEPTIDE | METH A | D-GAL | METH A | DIRECT | PRIMING | DIRECT | PRIMING |
| 17 | − | | + | − | | | |
| 13 | − | | − | + | | | |
| 14 | − | | + | + | | | |
| 15 | − | | − | − | | | |
| 18 | − | − | | | | | |
| 19 | + | | + | + | + | + | + |
| 20 | − | | − | − | | | |
| 21 | +* | | + | + | + | + | + |
| 22 | | + | + | + | + | | |
| 23 | + | + | + | + | | | |
| 24 | − | | − | − | | | |
| 25 | +/− | | − | + | | | |
| 26 | − | | − | + | | | |
| 4 | − | | | + | | | |
| 5 | − | | − | + | | | |
| 6 | − | | | − | | | |
| 3 | − | | | | | | |
| 28 | + | − | + | | | | |
| 29 | − | − | + | | | | |
| 30 | +* | + | + | | | | |
| 31 | + | + | − | | | | |
| 32 | − | | − | | | | |
| 33 | − | | +* | | | | |
| 34 | − | | +* | | | | |
| 36 | − | | − | | | | |
| 35 | + | | + | | | | |
| 27 | − | | − | | | | |
| 7 | − | | + | +* | | | |

Figure 7:
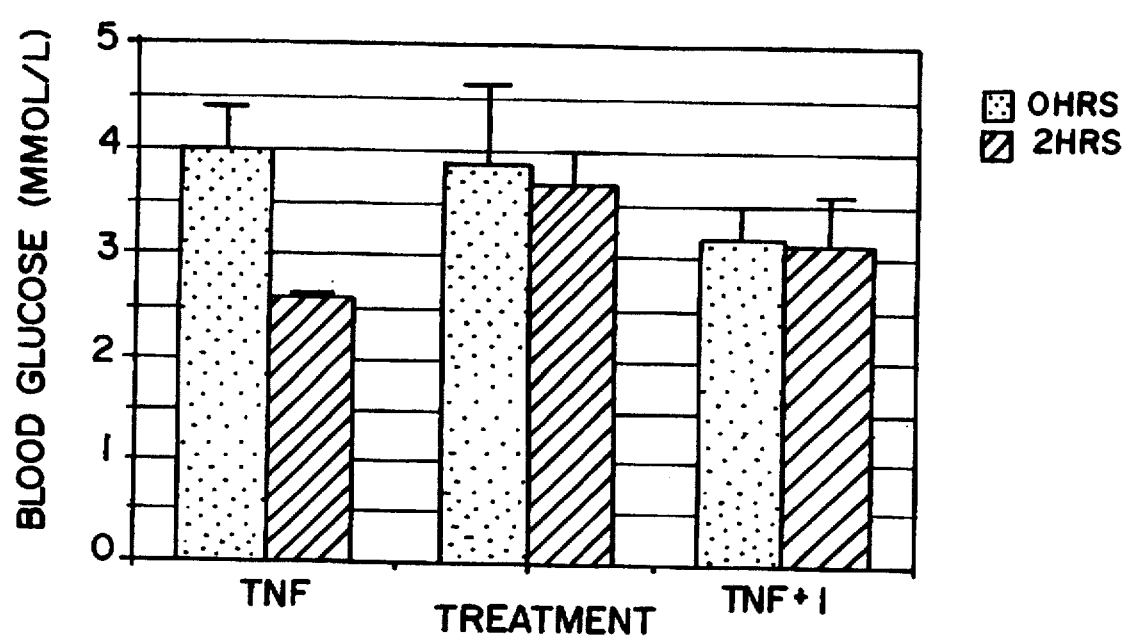
FIG. 7 shows the effect of Peptide 1 on TNF-induced decrease in blood glucose levels in mice administered with 200 μg TNF.

TNF administered at a dose of 200 μg was found to be toxic in mice according to the parameters studied. In particular, blood glucose levels had fallen by 120 minutes (FIG. 7) Peptide 1 alone in 2 of the 3 mice studied did not reduce blood glucose levels. Mouse 1 in this group recovered normal blood glucose levels within by 180 minutes. Mice in the group treated with a combination of TNF and Peptide 1 showed no reduction in blood glucose levels at 120 min and a small decrease at 180 min.

Figure 6:
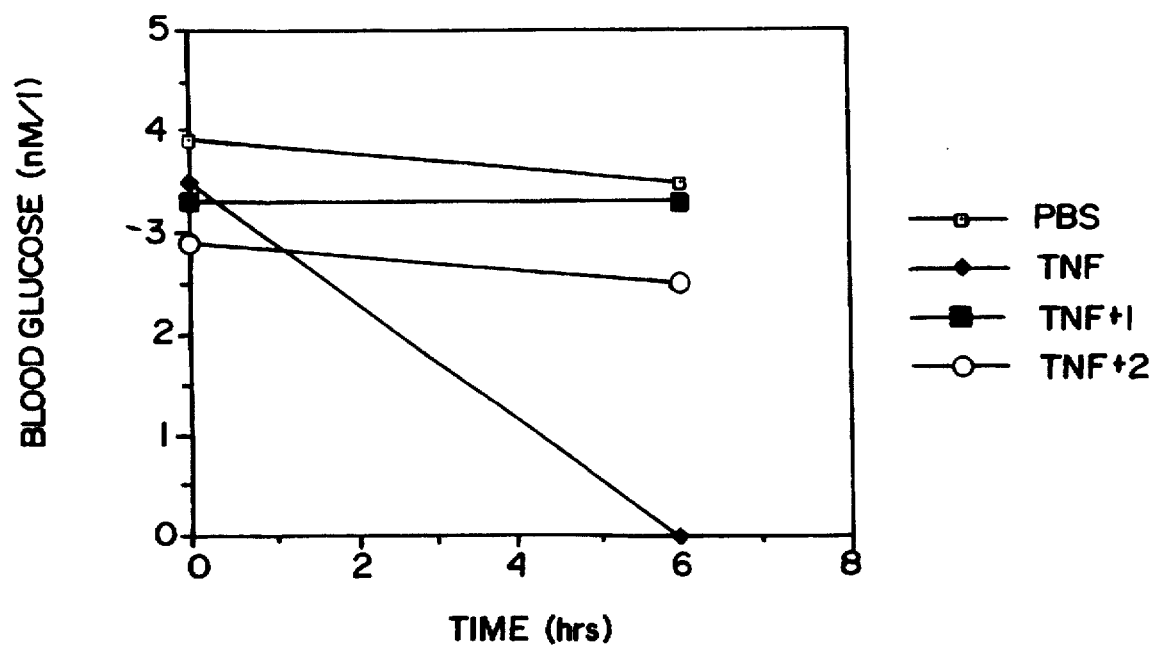

As shown in FIG. 6, 10 μg of Peptide 2 given to mice treated with 200 μg of recombinant human TNF abrogated TNF toxicity as indicated by the inhibition of blood glucose changes evident in mice treated with TNF alone.

Figure 12:
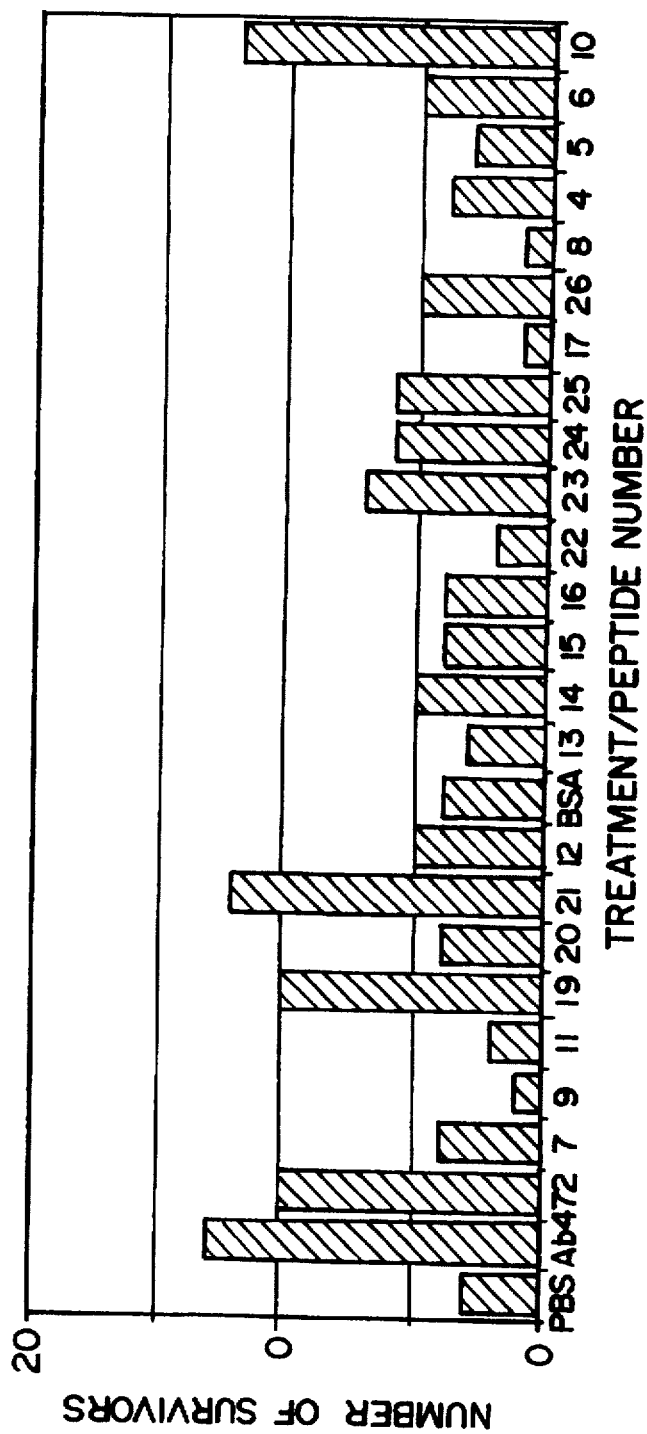
FIG. 12 shows the effect of peptides on TNF toxicity in Meth A ascites tumour-bearing mice (each group contains 20 animals; scored positive if 7 or more survived)
Figure 13:
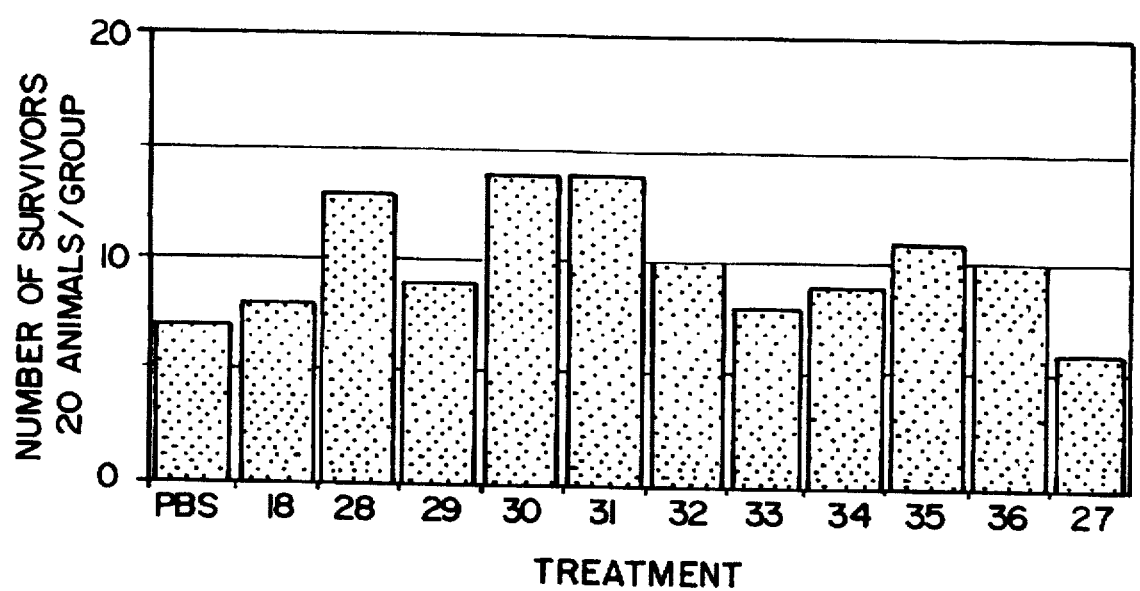
FIG. 13 shows the effect of peptides on TNF toxicity in Meth A ascites tumour-bearing mice (each group contains 20 animals: scored positive if 10 or more survived)
Figure 14:
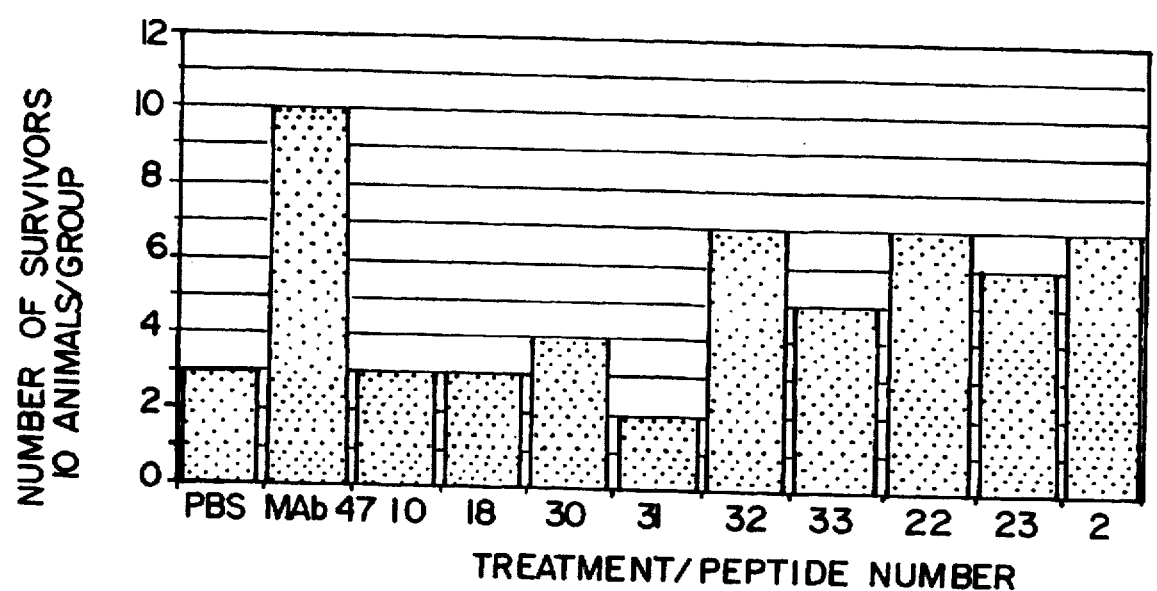
FIG. 14 shows effect of peptides on TNF toxicity in D-galactosamine sensitized mice (each group contains 10 animals: scored positive if 6 or more survive).
Figure 15:
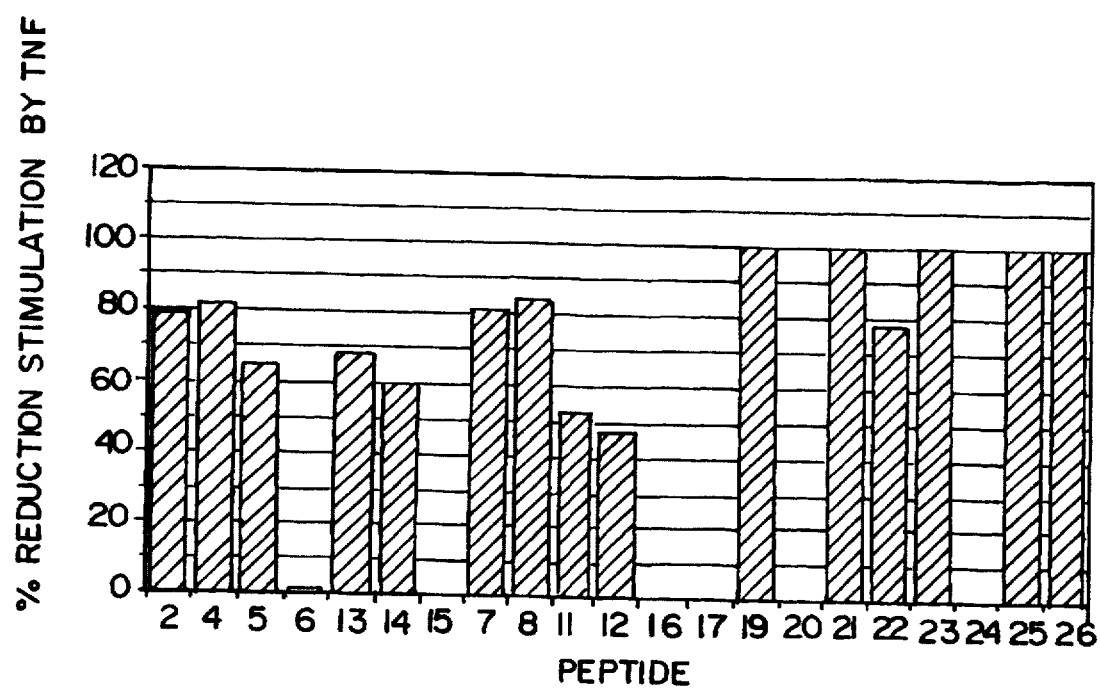
FIG. 15 shows the effect of peptides on direct induction of chemiluminescence by TNF on human neutrophils.
Figure 16:
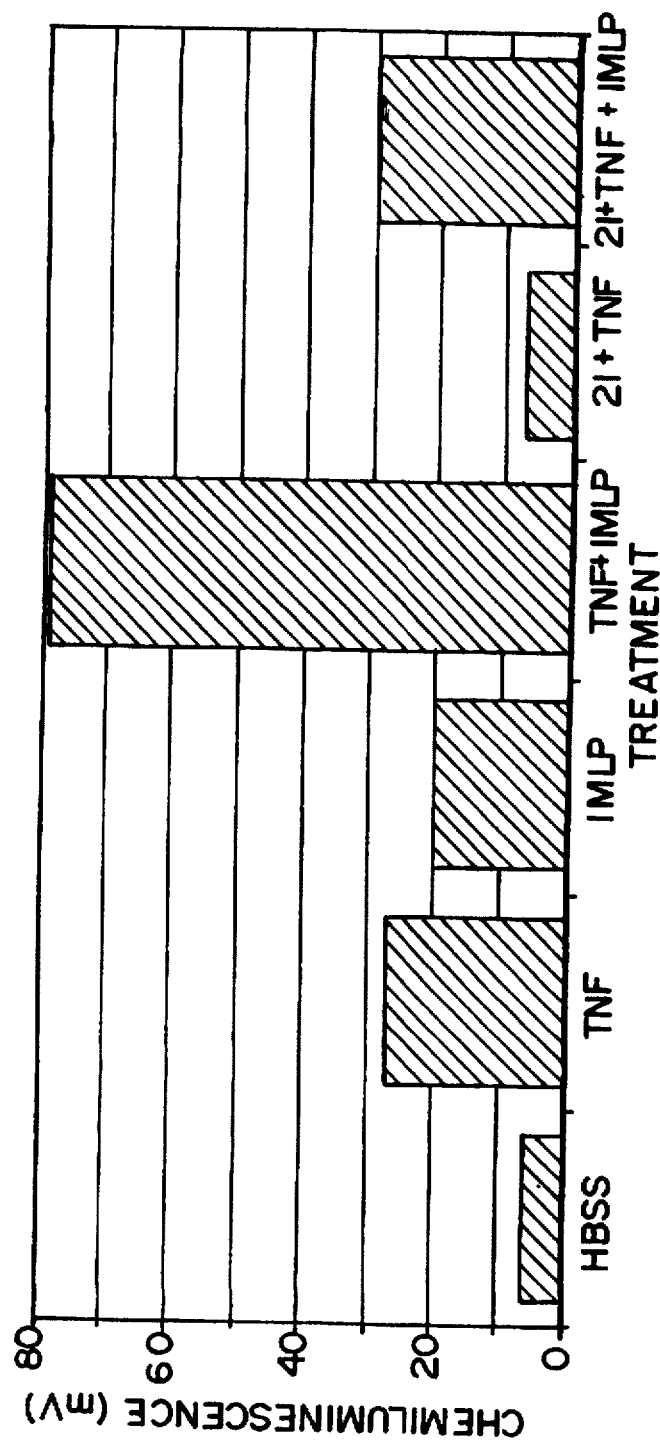
FIG. 16 shows inhibition of TNF priming of human neutrophils by Peptide 21.
Figure 17:
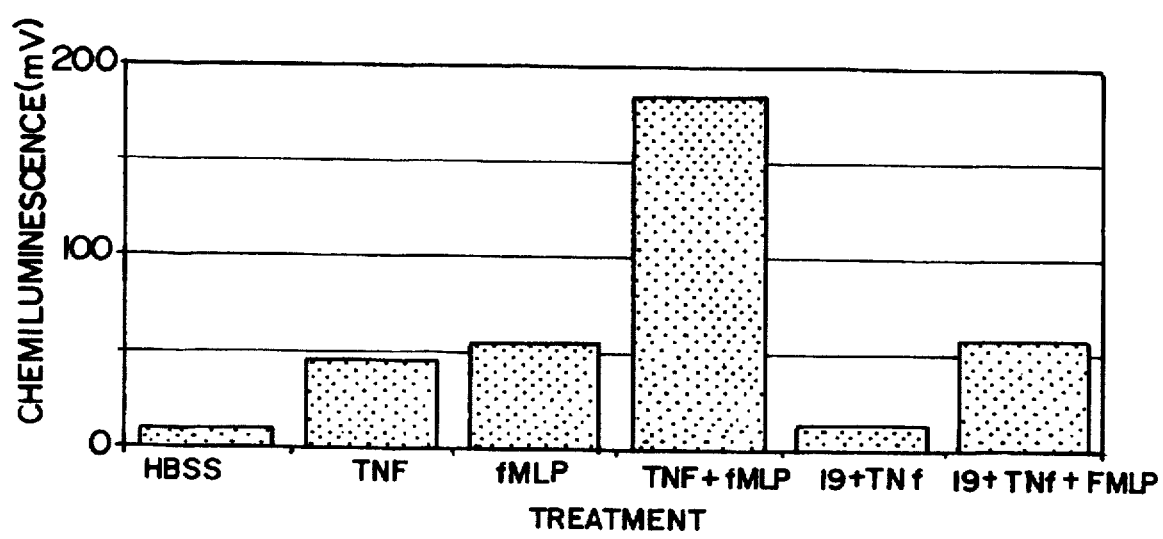
FIG. 17 shows inhibition of TNF priming of human neutrophils by Peptide 19.
Figure 18:
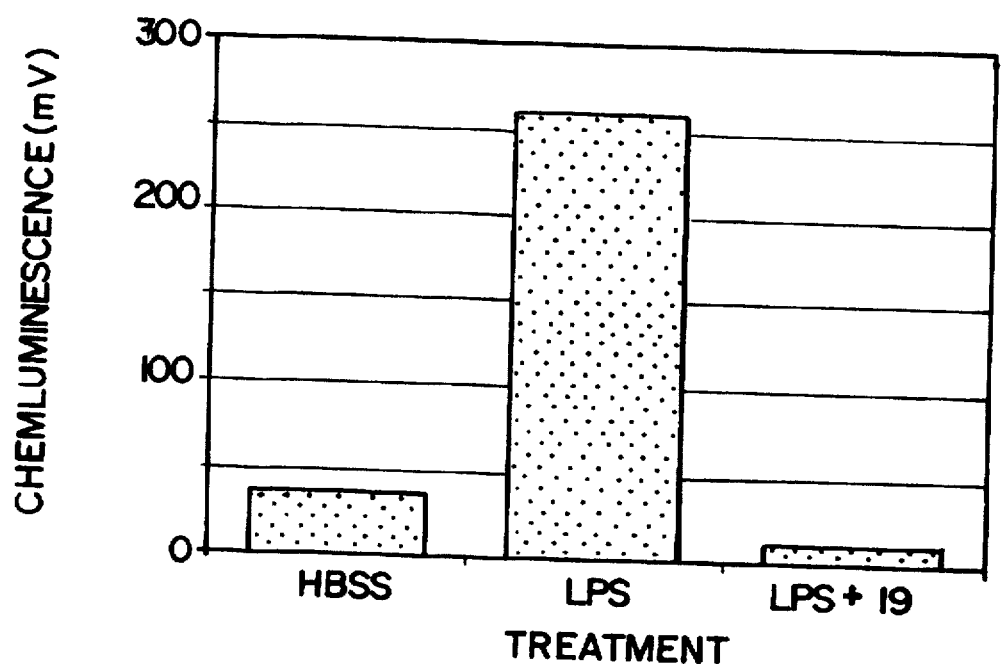
FIG. 18 shows inhibition of LPS stimulation of neutrophils by Peptide 19.
Figure 19:
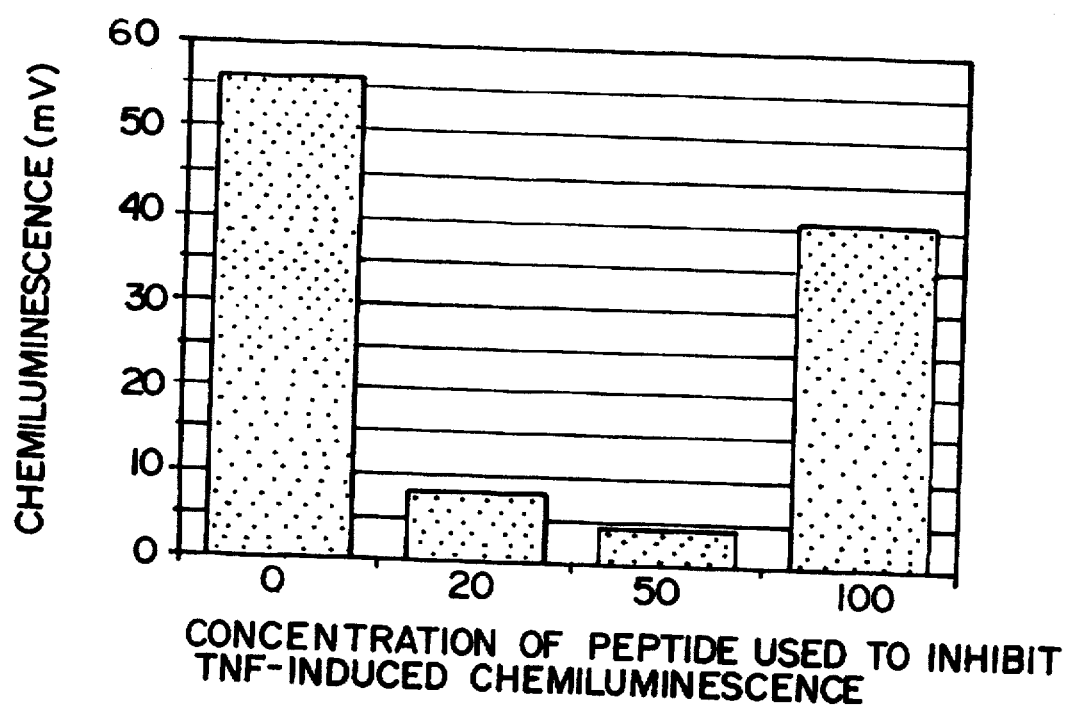
FIG. 19 shows dose-dependent effects of Peptide 9 on TNF-induced chemiluminescence.
Figure 20:
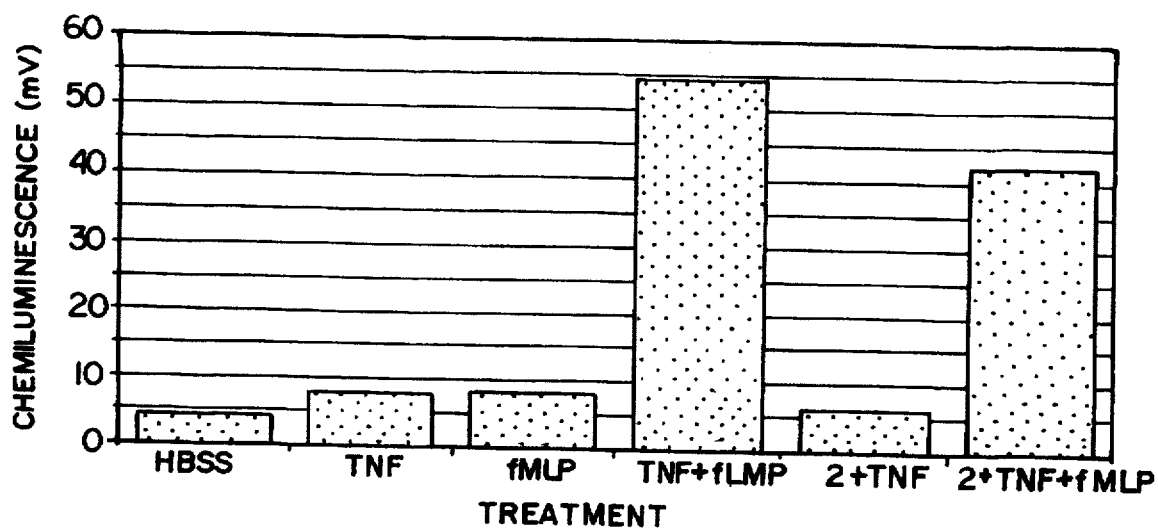
FIG. 20 shows effect of peptide 2 on human TNF priming of human neutrophils.
Figure 21:
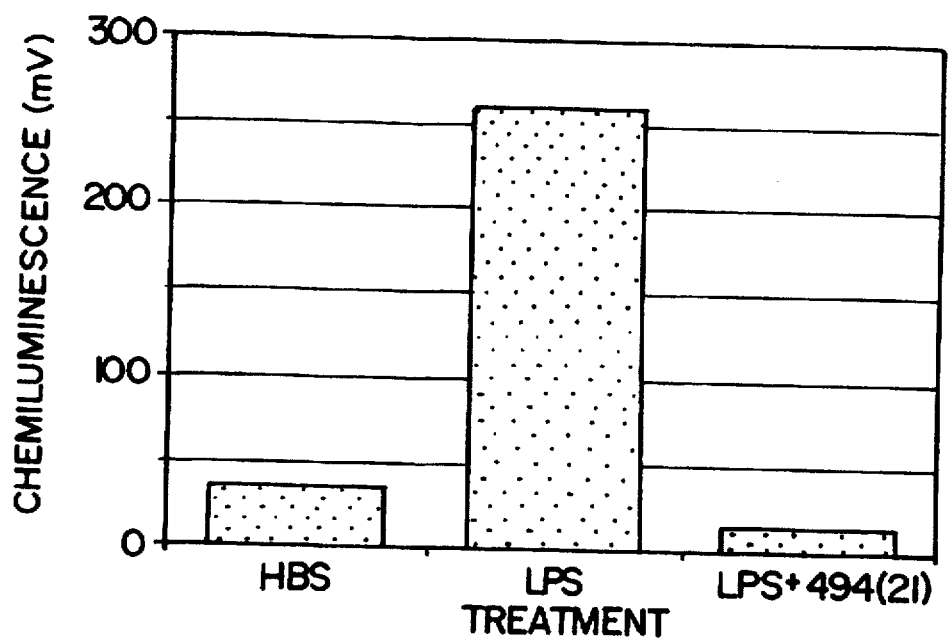
FIG. 21 shows inhibition of LPS-induced chemiluminescence response of human neutrophils by Peptide 21.
Figure 22:
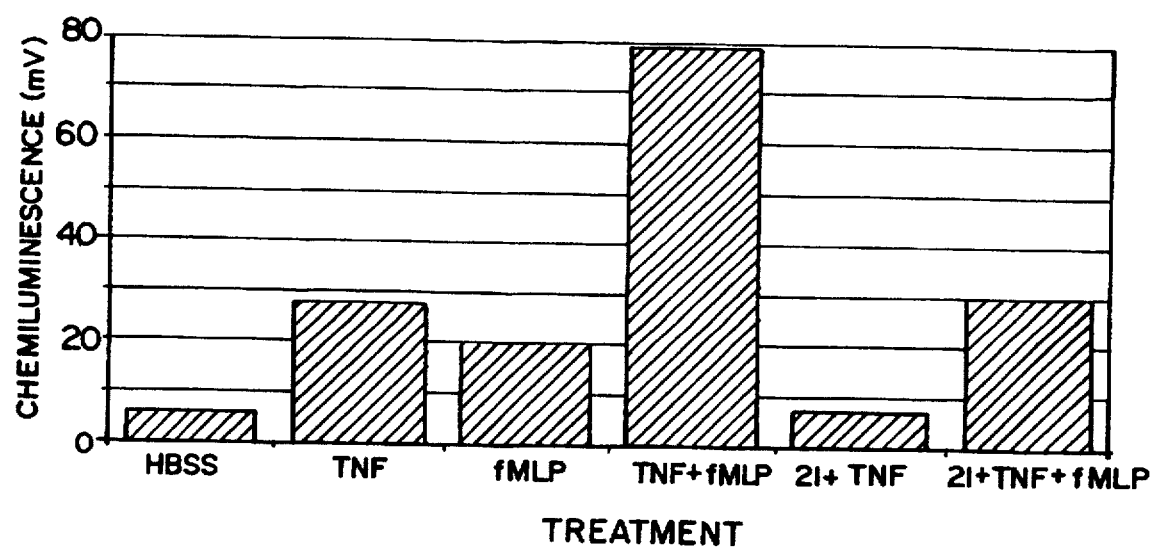
FIG. 22 shows inhibition of TNF priming of human neutrophils by Peptide 21.

When general appearance of treated mice was considered it was noted that all 3 TNF only treated mice had ruffled fur, touch sensitivity and light sensitivity. One mouse in this group also had diarrhoea. Mice treated with Peptide 1 alone showed only slight touch sensitivity with one mouse showing slight ruffling of the fur at 180 mins. Mice treated with a combination of TNF and Peptide 1 showed ruffling of the fur and slight touch sensitivity at 180 mins but failed to show either light sensitivity or onset of diarrhoea. In addition, Peptide 1 and related peptides prevented death in acute models of TNF lethality (FIGS. 12 & 13).

Peptide 1 failed to either activate the respiratory burst of human neutrophils (Table 5) or to induce procoagulant activity on bovine aortic endothelial cells, and hence is free of these negative aspects of TNF activity in acute or chronic inflammation. However, Peptide 1 and related peptides inhibited both the TNF and LPS-induced respiratory burst of human neutrophils (Figs- 15, 19, 18, 21A. Further, several peptides inhibited priming of the neutrophil response to a bacterially-derived peptide EMLP (FIGS. 16, 17, 20, 22).

TABLE 5

| | Concentration μg/$10^6$ cells | | | | |
|---|---|---|---|---|---|
| Peptide | 0 | 1 | 10 | 100 | 500 |
| 275 | 1.02 | 0.99 | 0.69 | 0.43 | 0.80 |
| 1 | 0.34 | 0.93 | 0.74 | 0.55 | 1.10 |
| 302 | 0.37 | 0.15 | 0.18 | 0.29 | |
| 303 | 0.37 | 0.22 | 0.17 | 0.22 | |
| 304 | 0.37 | 0.18 | 0.43 | 2.56 | 2.76 |
| 305 | 0.37 | 0.27 | 0.36 | 0.24 | |
| 306 | 0.37 | 0.27 | 0.35 | 0.23 | |
| 307 | 0.37 | 0.35 | 0.37 | 0.42 | |
| 323 | 0.37 | 0.23 | 0.17 | 0.47 | |
| 308 | 0.37 | 0.91 | 1.80 | 49.52 | |
| 309 | 0.37 | 0.38 | 0.98 | 13.44 | |

Results are expressed as mV of lucigenin dependent chemiluminescence and represent peak of response i.e. the maximal cell activity attained.

Figure 3:
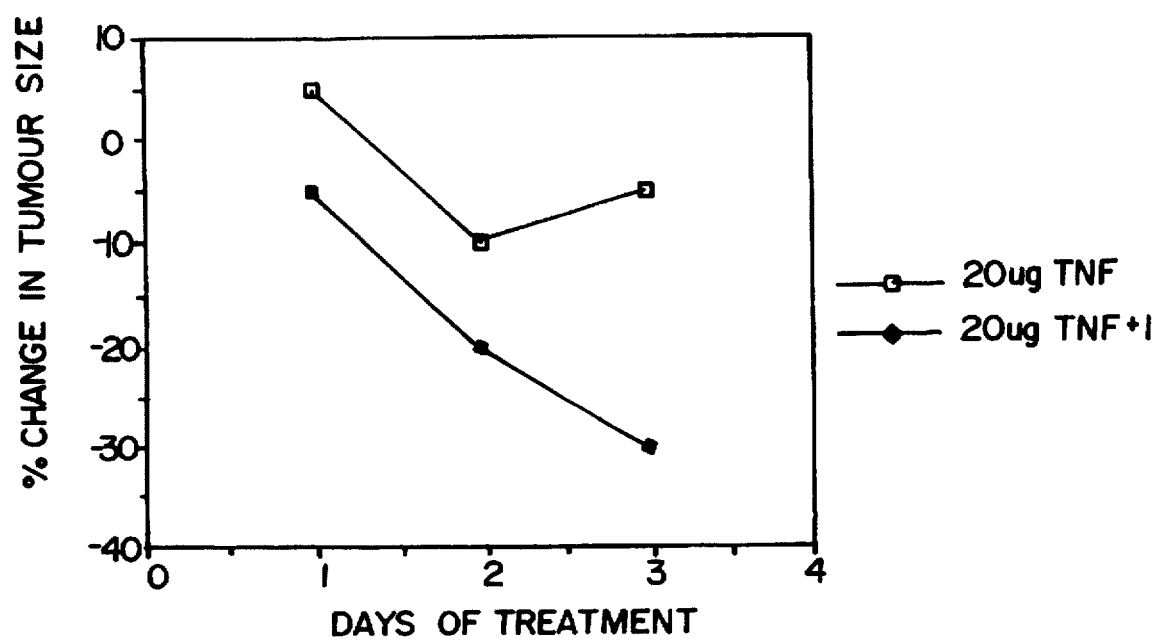
Figure 4:
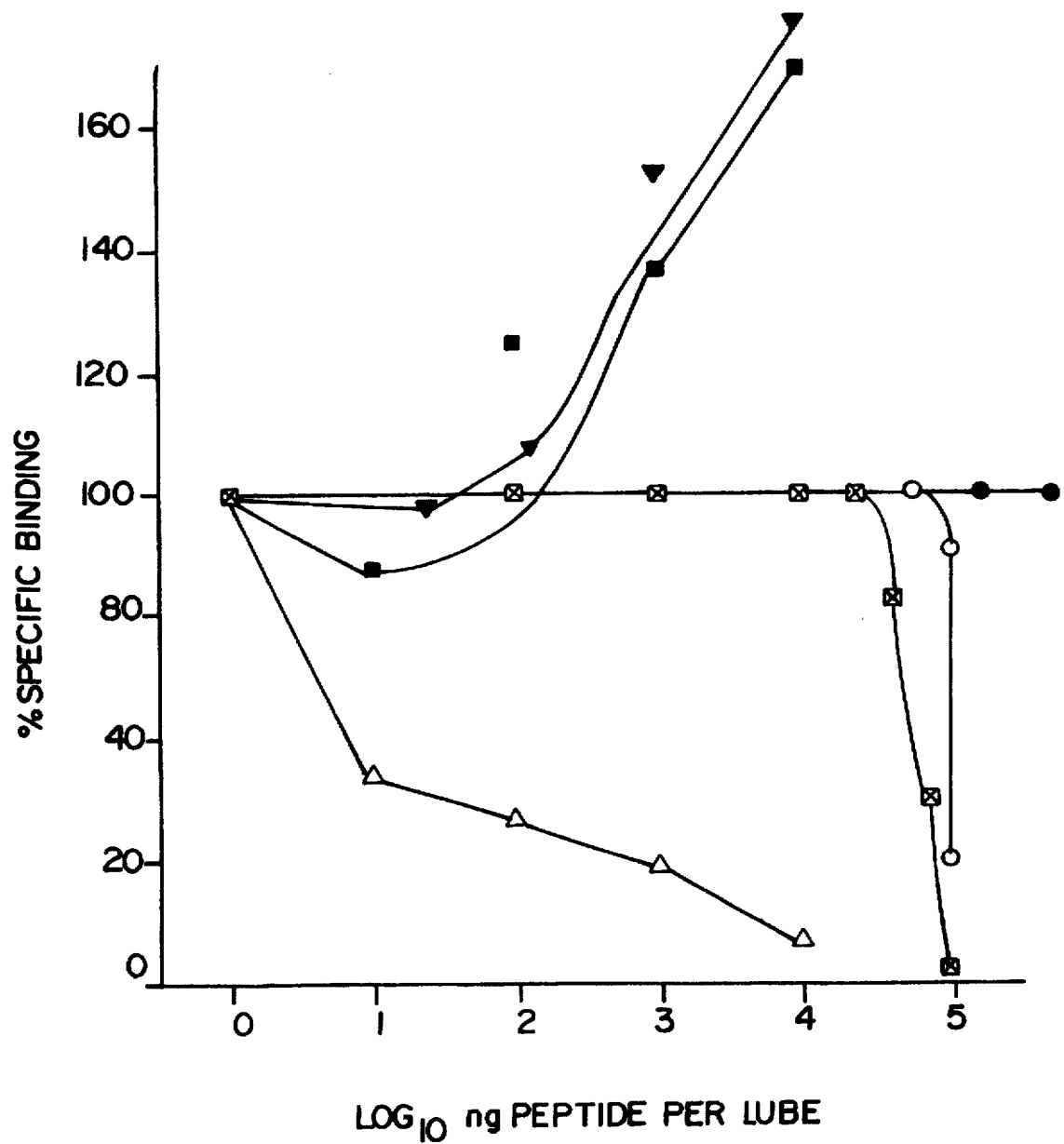
Figure 5:
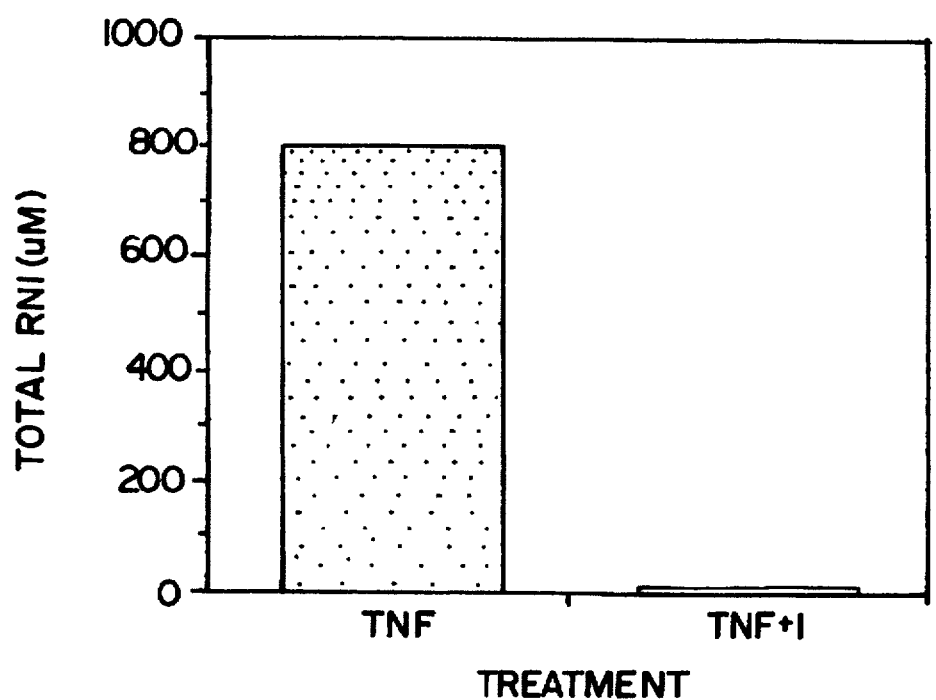

The results shown in FIG. 3 clearly show one of the desirable effects of TNFα, i.e. tumour regression, is unaffected by Peptide 1. Further, Peptide 1 does not inhibit binding of TN to tumour cell receptors (FIG. 4). Table 6 indicates that Peptide 1 is devoid of intrinsic anti-tumour activity. The ability of Peptide 1 to prevent high plasma RNI levels in TNFα treated malaria primed mice is also strongly indicative of the therapeutic usefulness of this peptide (FIG. 5). Peptide 1 also inhibits the TNF-induced decrease in blood glucose levels evident in mice treated with TNF alone (FIG. 2). Further in the experiments involving mice infected with malaria parasites; of the three mice treated with TNFα alone one died and the other two were moribund. In contrast in the group of three mice treated with TNFα and Peptide 1 all survived and none were moribund. This very marked result strongly indicates the potential usefulness of this peptide as a therapeutic.

Figure 8:
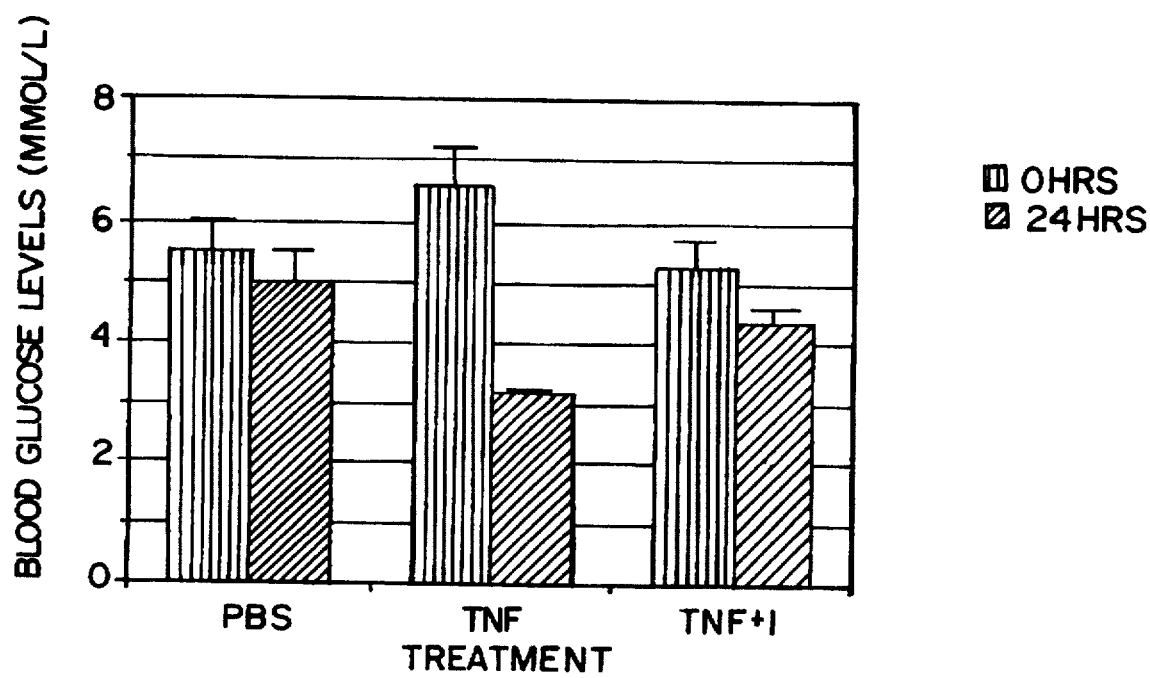
FIG. 8 shows the effect of Peptide 1 on TNF-induced decrease in blood glucose levels in ascites tumour-bearing mice.
Figure 9:
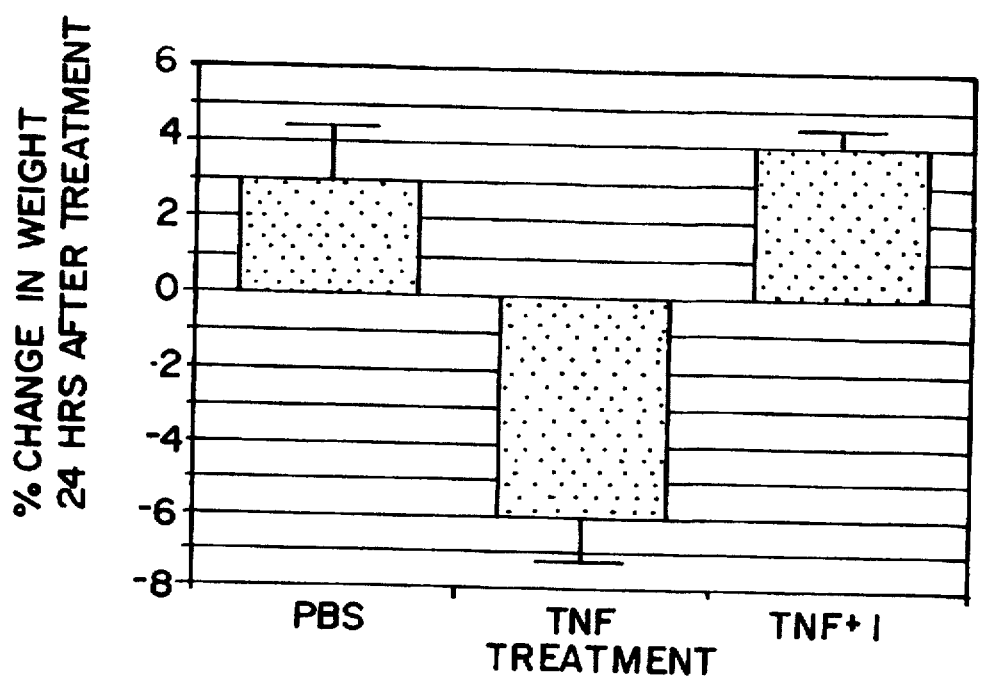
FIG. 9 shows the effect of Peptide 1 on TNF-induced weight loss in ascites tumour-bearing mice.
Figure 10:
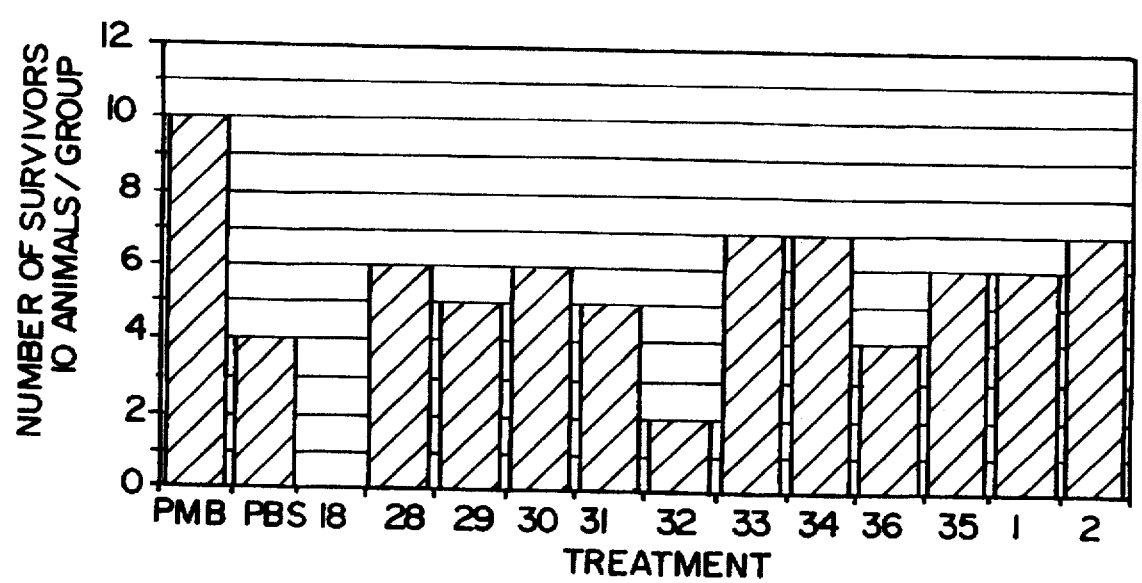
FIG. 10 shows the effect of peptides on LPS toxicity in Meth A ascites tumour-bearing mice (10 animals per group scored positive if 7 or more survive)
Figure 11:
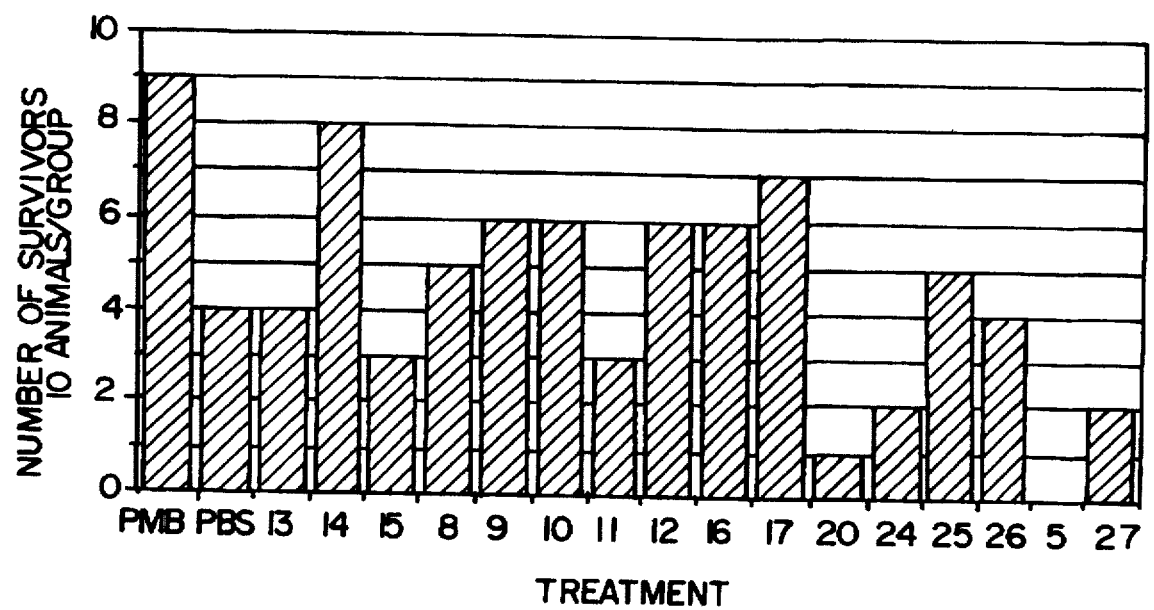
FIG. 11 shows the effect of peptides on LPS toxicity in Meth A ascites tumour-bearing mice (10 animals per group scored positive if 7 or more survive)

Paptide 1 inhibits not only the TNF-induced hypopglycaemia in sensitized mice but also in ascites tumor-bearing mice (FIG. 8). Further, tumour-bearing mice treated with TNF +Peptide 1 fail to develop the cachexia or weight loss associated with TNF treatment (FIG. 9).

As will be seen from the above information the peptide of the present invention are capable of abrogating TNF and/or LPS toxicity in vivo and neutrophil activation by LPS or TNF in vitro. This peptide has utility in the treatment of numerous disease states which are due to the deleterious effects of TNF and/or LPS.

TABLE 6

In vitro cytotoxicity of TNF and synthetic TNF peptides on WEHI 164 fibrosarcoma cells

| TNF/PEPTIDE | % VIABLE CELLS* |
| --- | --- |
| TNF# | 26.6 |
| 275+ | 100 |
| 1 | 100 |
| 302 | 48.7 |
| 304 | 100 |
| 305 | 72.7 |

TABLE 6-continued

In vitro cytotoxicity of TNF and synthetic TNF peptides on WEHI 164 fibrosarcoma cells

| TNF/PEPTIDE | % VIABLE CELLS* |
| --- | --- |
| 306 | 100 |
| 307 | 100 |
| 308 | 42.2 |
| 309 | 92.8 |

*% Viability was determined by comparison with untreated control cells. Results shown are the means of quadruplicate determinations.
TNF was at 50 units per culture which is equivalent to 3 ug (12 ug/ml)
+Each peptide was tested at 50 ug/culture (200 ug/ml)

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

We claim:
1. A peptide selected from the group consisting of:

Arg-Thr-Pro-Ser-Ala-Lys-Pro-Val-Ala-His-Val-Val-Ala; SEQ ID NO:19 Arg-Thr-Pro-Ser-Lys-Asp-Pro-Val-Ala-His-Val-Val-Ala; SEQ ID NO:21 Val-Arg-Ser-Ser-Ser-Arg-Thr-Pro-Ser-Asp-Lys-Pro-Val-Ala-Arg-Val-Val-Ala;

SEQ ID NO:22 Val-Arg-Ser-Ser-Ser-Arg-Thr-Pro-Ser-Asp-Lys-Pro-Val-Ala-Gln-Val-Val-Ala;

SEQ ID NO:23 Ac-Arg-Thr-Pro-Ser-Asp-Lys-Pro-Val-Ala-His-Val-NH2; SEQ ID NO:7 Arg-Thr-Pro-Ser-Asp-Lys-Pro-Val-Ala-Ala-Val; SEQ ID NO:33 Arg-Thr-Pro-Ser-Asp-Lys-Pro-Val-Ala-Lys-Val; SEQ ID NO:34 Arg-Thr-Pro-Ser-Asp-Lys-Pro-Val-Ala-His-Val-Val; SEQ ID NO:8 Pro-Ser-Asp-Lys-Pro-Val-Ala-His-Val; SEQ ID NO:9 Pro-Ser-Asp-Lys-Pro-Val-Ala-His; SEQ ID NO: 10 Pro-Ser-Asp-Lys-Pro-Val; SEQ ID NO: 12 Val-Arg-Ser-Ser-Ser-Arg-Thr-Pro-Ser-Asp-Lys-Pro-Val-Val-His-Val-Val-Ala;

SEQ ID NO:25 Arg-Thr-Pro-Ser-Asp-Lys-Pro-Val-Ala-His-Val-Val-Ala-Asn-Pro-Gln-Ala-Glu-Gly-Gln-Leu; SEQ ID NO:26 Val-Arg-Ser-Ser-Ser-Arg-Thr-Pro-Ser-Asp; SEQ ID NO:28 Ac-Pro-Ser-Asp-Lys-Pro-Val-Ala-NH2; SEQ ID NO: 11 Arg-Thr-Pro-Ser-Asp-Lys-Pro-Val-Ala-Asp-Val; SEQ ID NO:35 Val-Arg-Ser-Ser-Ser-Arg-Thr-Pro-Ser-Asp-Lys-Pro-Val-Ala-His-Val-Val-Ala-Asn-Pro-Gln-Ala-Glu-Gly-Gln-Leu; SEQ ID NO:4 Asp-Lys-Pro-Val-Ala-His-Val-Val-Ala; SEQ ID NO:5 Arg-Thr-Pro-Ser-Asp-Lys-Pro-Val-Ala-His-Val; SEQ ID NO:7 Thr-Pro-Ser-Asp-Lys-Pro-Val-Ala-His-Val-Val-Ala; SEQ ID NO: 13 Pro-Ser-Asp-Lys-Pro-Val-Ala-His-Val-Val-Ala; SEQ ID NO:14 Pro-Val-Ala-His-Val-Val-Ala; SEQ ID NO: 17 and Arg-Thr-Pro-Ser-Asp-Lys-Pro-Val-Val-His-Val SEQ ID NO:31.

2. A peptide as claimed in claim 1, in which the peptide is Val-Arg-Ser-Ser-Ser-Arg-Thr-Pro-Ser-Asp; SEQ ID NO:28 Arg-Thr-Pro-Ser-Ala-Lys-Pro-Val-Ala-His-Val-Val-Ala; SEQ ID NO: 19 Arg-Thr-Pro-Ser-Lys-Asp-Pro-Val-Ala-His-Val-Val-Ala; SEQ ID NO:21 Val-Arg-Ser-Ser-Ser-Arg-Thr-Pro-Ser-Asp-Lys-Pro-Val-Ala-Arg-Val-Val-Ala;

SEQ ID NO:22 Val-Arg-Ser-Ser-Ser-Arg-Thr-Pro-Ser-Asp-Lys-Pro-Val-Ala-Gln-Val-Val-Ala;

SEQ ID NO:23 or Arg-Thr-Pro-Ser-Asp-Lys-Pro-Val-Ala-Asp-Val SEQ ID NO:35.

3. A pharmaceutical composition for use in treating subjects suffering from acute or chronic inflammation, the composition comprising a therapeutically effective amount of a peptide as claimed in claims 1 to and a pharmaceutically acceptable sterile carrier.

4. A composition as claimed in claim 3 in which the composition is for administration topically, as a nasal spray, ocularly, intraveneously, intraperitoneally, intramuscularly, subcutaneously or for oral delivery.

5. A composition as claimed in claim 3 or in which the composition provides slow release of the active peptide.

6. A method of treating a subject suffering from acute or chronic inflammation, the method comprising administering to the subject the composition as claimed in claim 3.

* * * * *

SEQUENCE LISTING ( 1 ) GENERAL INFORMATION:

( i i i ) NUMBER OF SEQUENCES: 47

( 2 ) INFORMATION FOR SEQ ID NO:1:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: both ( i i ) MOLECULE TYPE: peptide ( x i ) SEQUENCE DESCRIPTION: SEQ ID NO:1:

```
Val Arg Ser Ser Ser Arg Thr Pro Ser Asp Lys Pro Val Ala His
1               5                   10                  15
Val Val Ala
```

( 2 ) INFORMATION FOR SEQ ID NO:2:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: both ( i i ) MOLECULE TYPE: peptide ( x i ) SEQUENCE DESCRIPTION: SEQ ID NO:2:

```
Arg Thr Pro Ser Asp Lys Pro Val Ala His Val Val Ala
1               5                   10
```

( 2 ) INFORMATION FOR SEQ ID NO:3:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: both ( i i ) MOLECULE TYPE: peptide ( x i ) SEQUENCE DESCRIPTION: SEQ ID NO:3:

Arg Ser Ser Ser Arg Thr Pro Ser Asp Lys Pro Val Ala His
1               5                   10

( 2 ) INFORMATION FOR SEQ ID NO:4:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: both ( i i ) MOLECULE TYPE: peptide ( x i ) SEQUENCE DESCRIPTION: SEQ ID NO:4:

Val Arg Ser Ser Ser Arg Thr Pro Ser Asp Lys Pro Val Ala His
1               5                   10                  15

Val Val Ala Asn Pro Gln Ala Glu Gly Gln Leu
                20              25

( 2 ) INFORMATION FOR SEQ ID NO:5:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: both ( i i ) MOLECULE TYPE: peptide ( x i ) SEQUENCE DESCRIPTION: SEQ ID NO:5:

Asp Lys Pro Val Ala His Val Val Ala
1               5

( 2 ) INFORMATION FOR SEQ ID NO:6:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: both ( i i ) MOLECULE TYPE: peptide ( x i ) SEQUENCE DESCRIPTION: SEQ ID NO:6:

His Val Val Ala Asn Pro Gln Ala
1               5

( 2 ) INFORMATION FOR SEQ ID NO:7:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: both ( i i ) MOLECULE TYPE: peptide ( x i ) SEQUENCE DESCRIPTION: SEQ ID NO:7:

Arg Thr Pro Ser Asp Lys Pro Val Ala His Val
1               5                   10

( 2 ) INFORMATION FOR SEQ ID NO:8:

( i ) SEQUENCE CHARACTERISTICS:
        ( A ) LENGTH: 12 amino acids ( B ) TYPE: amino acid
                    ( C ) STRANDEDNESS: single
                    ( D ) TOPOLOGY: both ( i i ) MOLECULE TYPE: peptide ( x i ) SEQUENCE DESCRIPTION: SEQ ID NO:8:

Arg Thr Pro Ser Asp Lys Pro Val Ala His Val Val
1               5                   10

( 2 ) INFORMATION FOR SEQ ID NO:9:

( i ) SEQUENCE CHARACTERISTICS:
                    ( A ) LENGTH: 9 amino acids
                    ( B ) TYPE: amino acid
                    ( C ) STRANDEDNESS: single
                    ( D ) TOPOLOGY: both ( i i ) MOLECULE TYPE: peptide ( x i ) SEQUENCE DESCRIPTION: SEQ ID NO:9:

Pro Ser Asp Lys Pro Val Ala His Val
1               5

( 2 ) INFORMATION FOR SEQ ID NO:10:

( i ) SEQUENCE CHARACTERISTICS:
                    ( A ) LENGTH: 8 amino acids
                    ( B ) TYPE: amino acid
                    ( C ) STRANDEDNESS: single
                    ( D ) TOPOLOGY: both ( i i ) MOLECULE TYPE: peptide ( x i ) SEQUENCE DESCRIPTION: SEQ ID NO:10:

Pro Ser Asp Lys Pro Val Ala His
1               5

( 2 ) INFORMATION FOR SEQ ID NO:11:

( i ) SEQUENCE CHARACTERISTICS:
                    ( A ) LENGTH: 7 amino acids
                    ( B ) TYPE: amino acid
                    ( C ) STRANDEDNESS: single
                    ( D ) TOPOLOGY: both ( i i ) MOLECULE TYPE: peptide ( x i ) SEQUENCE DESCRIPTION: SEQ ID NO:11:

Pro Ser Asp Lys Pro Val Ala
1               5

( 2 ) INFORMATION FOR SEQ ID NO:12:

( i ) SEQUENCE CHARACTERISTICS:
                    ( A ) LENGTH: 6 amino acids
                    ( B ) TYPE: amino acid
                    ( C ) STRANDEDNESS: single
                    ( D ) TOPOLOGY: both ( i i ) MOLECULE TYPE: peptide ( x i ) SEQUENCE DESCRIPTION: SEQ ID NO:12:

Pro Ser Asp Lys Pro Val
1               5

( 2 ) INFORMATION FOR SEQ ID NO:13:

( i ) SEQUENCE CHARACTERISTICS:
                    ( A ) LENGTH: 12 amino acids (B) TYPE: amino acid
(C) STRANDEDNESS: single
(D) TOPOLOGY: both (ii) MOLECULE TYPE: peptide (xi) SEQUENCE DESCRIPTION: SEQ ID NO:13:

Thr Pro Ser Asp Lys Pro Val Ala His Val Val Ala
1               5                   10

(2) INFORMATION FOR SEQ ID NO:14:

(i) SEQUENCE CHARACTERISTICS:
    (A) LENGTH: 11 amino acids
    (B) TYPE: amino acid
    (C) STRANDEDNESS: single
    (D) TOPOLOGY: both (ii) MOLECULE TYPE: peptide (xi) SEQUENCE DESCRIPTION: SEQ ID NO:14:

Pro Ser Asp Lys Pro Val Ala His Val Val Ala
1               5                   10

(2) INFORMATION FOR SEQ ID NO:15:

(i) SEQUENCE CHARACTERISTICS:
    (A) LENGTH: 10 amino acids
    (B) TYPE: amino acid
    (C) STRANDEDNESS: single
    (D) TOPOLOGY: both (ii) MOLECULE TYPE: peptide (xi) SEQUENCE DESCRIPTION: SEQ ID NO:15:

Ser Asp Lys Pro Val Ala His Val Val Ala
1               5                   10

(2) INFORMATION FOR SEQ ID NO:16:

(i) SEQUENCE CHARACTERISTICS:
    (A) LENGTH: 8 amino acids
    (B) TYPE: amino acid
    (C) STRANDEDNESS: single
    (D) TOPOLOGY: both (ii) MOLECULE TYPE: peptide (xi) SEQUENCE DESCRIPTION: SEQ ID NO:16:

Lys Pro Val Ala His Val Val Ala
1               5

(2) INFORMATION FOR SEQ ID NO:17:

(i) SEQUENCE CHARACTERISTICS:
    (A) LENGTH: 7 amino acids
    (B) TYPE: amino acid
    (C) STRANDEDNESS: single
    (D) TOPOLOGY: both (ii) MOLECULE TYPE: peptide (xi) SEQUENCE DESCRIPTION: SEQ ID NO:17:

Pro Val Ala His Val Val Ala
1               5

(2) INFORMATION FOR SEQ ID NO:18:

(i) SEQUENCE CHARACTERISTICS:
    (A) LENGTH: 7 amino acids ( B ) TYPE: amino acid
( C ) STRANDEDNESS: single
( D ) TOPOLOGY: both ( i i ) MOLECULE TYPE: peptide ( x i ) SEQUENCE DESCRIPTION: SEQ ID NO:18:

Pro Val Ala His Val Val Ala
1               5

( 2 ) INFORMATION FOR SEQ ID NO:19:

( i ) SEQUENCE CHARACTERISTICS:
( A ) LENGTH: 13 amino acids
( B ) TYPE: amino acid
( C ) STRANDEDNESS: single
( D ) TOPOLOGY: both ( i i ) MOLECULE TYPE: peptide ( x i ) SEQUENCE DESCRIPTION: SEQ ID NO:19:

Arg Thr Pro Ser Ala Lys Pro Val Ala His Val Val Ala
1               5                   10

( 2 ) INFORMATION FOR SEQ ID NO:20:

( i ) SEQUENCE CHARACTERISTICS:
( A ) LENGTH: 13 amino acids
( B ) TYPE: amino acid
( C ) STRANDEDNESS: single
( D ) TOPOLOGY: both ( i i ) MOLECULE TYPE: peptide ( x i ) SEQUENCE DESCRIPTION: SEQ ID NO:20:

Arg Thr Pro Ser Asp Ala Pro Val Ala His Val Val Ala
1               5                   10

( 2 ) INFORMATION FOR SEQ ID NO:21:

( i ) SEQUENCE CHARACTERISTICS:
( A ) LENGTH: 13 amino acids
( B ) TYPE: amino acid
( C ) STRANDEDNESS: single
( D ) TOPOLOGY: both ( i i ) MOLECULE TYPE: peptide ( x i ) SEQUENCE DESCRIPTION: SEQ ID NO:21:

Arg Thr Pro Ser Lys Asp Pro Val Ala His Val Val Ala
1               5                   10

( 2 ) INFORMATION FOR SEQ ID NO:22:

( i ) SEQUENCE CHARACTERISTICS:
( A ) LENGTH: 18 amino acids
( B ) TYPE: amino acid
( C ) STRANDEDNESS: single
( D ) TOPOLOGY: both ( i i ) MOLECULE TYPE: peptide ( x i ) SEQUENCE DESCRIPTION: SEQ ID NO:22:

Val Arg Ser Ser Ser Arg Thr Pro Ser Asp Lys Pro Val Ala Arg
1               5                   10                  15

Val Val Ala ( 2 ) INFORMATION FOR SEQ ID NO:23:

( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: both ( i i ) MOLECULE TYPE: peptide ( x i ) SEQUENCE DESCRIPTION: SEQ ID NO:23:

Val Arg Ser Ser Ser Arg Thr Pro Ser Asp Lys Pro Val Ala Gln
1               5                   10                  15

Val Val Ala ( 2 ) INFORMATION FOR SEQ ID NO:24:

( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: both ( i i ) MOLECULE TYPE: peptide ( x i ) SEQUENCE DESCRIPTION: SEQ ID NO:24:

Val Arg Ser Ser Ser Arg Thr Pro Ser Asp Lys Pro Val Leu His
1               5                   10                  15

Val Val Ala ( 2 ) INFORMATION FOR SEQ ID NO:25:

( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: both ( i i ) MOLECULE TYPE: peptide ( x i ) SEQUENCE DESCRIPTION: SEQ ID NO:25:

Val Arg Ser Ser Ser Arg Thr Pro Ser Asp Lys Pro Val Val His
1               5                   10                  15

Val Val Ala ( 2 ) INFORMATION FOR SEQ ID NO:26:

( i ) SEQUENCE CHARACTERISTICS:
    ( A ) LENGTH: 21 amino acids
    ( B ) TYPE: amino acid
    ( C ) STRANDEDNESS: single
    ( D ) TOPOLOGY: both ( i i ) MOLECULE TYPE: peptide ( x i ) SEQUENCE DESCRIPTION: SEQ ID NO:26:

Arg Thr Pro Ser Asp Lys Pro Val Ala His Val Val Ala Asn Pro
1               5                   10                  15

Gln Ala Glu Gly Gln Leu
                20

( 2 ) INFORMATION FOR SEQ ID NO:27:

( i ) SEQUENCE CHARACTERISTICS:
    ( A ) LENGTH: 16 amino acids
    ( B ) TYPE: amino acid
    ( C ) STRANDEDNESS: single
    ( D ) TOPOLOGY: both ( i i ) MOLECULE TYPE: peptide ( x i ) SEQUENCE DESCRIPTION: SEQ ID NO:27:

Val Arg Ser Ser Ser Arg Thr Pro Ser Asp Lys Pro Val Ala His
1               5                   10                  15
Val ( 2 ) INFORMATION FOR SEQ ID NO:28:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: both ( i i ) MOLECULE TYPE: peptide ( x i ) SEQUENCE DESCRIPTION: SEQ ID NO:28:

Val Arg Ser Ser Ser Arg Thr Pro Ser Asp
1               5                   10

( 2 ) INFORMATION FOR SEQ ID NO:29:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: both ( i i ) MOLECULE TYPE: peptide ( x i ) SEQUENCE DESCRIPTION: SEQ ID NO:29:

Pro Ser Asp Lys Pro Val Ala
1               5

( 2 ) INFORMATION FOR SEQ ID NO:30:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: both ( i i ) MOLECULE TYPE: peptide ( x i ) SEQUENCE DESCRIPTION: SEQ ID NO:30:

Arg Thr Pro Ser Asp Lys Pro Val Ala His Val
1               5                   10

( 2 ) INFORMATION FOR SEQ ID NO:31:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: both ( i i ) MOLECULE TYPE: peptide ( x i ) SEQUENCE DESCRIPTION: SEQ ID NO:31:

Arg Thr Pro Ser Asp Lys Pro Val Val His Val
1               5                   10

( 2 ) INFORMATION FOR SEQ ID NO:32:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: both ( i i ) MOLECULE TYPE: peptide ( x i ) SEQUENCE DESCRIPTION: SEQ ID NO:32:

Arg Thr Pro Ser Asp Lys Pro Val Ala His Ala
1               5                   10

( 2 ) INFORMATION FOR SEQ ID NO:33:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: both ( i i ) MOLECULE TYPE: peptide ( x i ) SEQUENCE DESCRIPTION: SEQ ID NO:33:

Arg Thr Pro Ser Asp Lys Pro Val Ala Ala Val
1               5                   10

( 2 ) INFORMATION FOR SEQ ID NO:34:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: both ( i i ) MOLECULE TYPE: peptide ( x i ) SEQUENCE DESCRIPTION: SEQ ID NO:34:

Arg Thr Pro Ser Asp Lys Pro Val Ala Lys Val
1               5                   10

( 2 ) INFORMATION FOR SEQ ID NO:35:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: both ( i i ) MOLECULE TYPE: peptide ( x i ) SEQUENCE DESCRIPTION: SEQ ID NO:35:

Arg Thr Pro Ser Asp Lys Pro Val Ala Asp Val
1               5                   10

( 2 ) INFORMATION FOR SEQ ID NO:36:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: both ( i i ) MOLECULE TYPE: peptide ( x i ) SEQUENCE DESCRIPTION: SEQ ID NO:36:

Arg Thr Pro Ser Asp Lys Pro Val Ala His Val
1               5                   10

( 2 ) INFORMATION FOR SEQ ID NO:37:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: both (ii) MOLECULE TYPE: peptide (xi) SEQUENCE DESCRIPTION: SEQ ID NO:37:

Ala Lys Pro Trp Tyr Glu Pro Ile Tyr Leu
1               5                   10

(2) INFORMATION FOR SEQ ID NO:38:

(i) SEQUENCE CHARACTERISTICS:
    (A) LENGTH: 16 amino acids
    (B) TYPE: amino acid
    (C) STRANDEDNESS: single
    (D) TOPOLOGY: both (ii) MOLECULE TYPE: peptide (xi) SEQUENCE DESCRIPTION: SEQ ID NO:38:

Leu Arg Asp Asn Gln Leu Val Val Pro Ser Glu Gly Leu Tyr Leu
1               5                   10                  15

Ile (2) INFORMATION FOR SEQ ID NO:39:

(i) SEQUENCE CHARACTERISTICS:
    (A) LENGTH: 16 amino acids
    (B) TYPE: amino acid
    (C) STRANDEDNESS: single
    (D) TOPOLOGY: both (ii) MOLECULE TYPE: peptide (xi) SEQUENCE DESCRIPTION: SEQ ID NO:39:

Leu Ser Ala Ile Lys Ser Pro Lys Gln Arg Glu Thr Pro Glu Gly
1               5                   10                  15

Ala (2) INFORMATION FOR SEQ ID NO:40:

(i) SEQUENCE CHARACTERISTICS:
    (A) LENGTH: 21 amino acids
    (B) TYPE: amino acid
    (C) STRANDEDNESS: single
    (D) TOPOLOGY: both (ii) MOLECULE TYPE: peptide (xi) SEQUENCE DESCRIPTION: SEQ ID NO:40:

Leu Phe Lys Gly Gln Gly Cys Pro Ser Thr His Val Leu Leu Thr
1               5                   10                  15

His Thr Ile Ser Arg Ile
                20

(2) INFORMATION FOR SEQ ID NO:41:

(i) SEQUENCE CHARACTERISTICS:
    (A) LENGTH: 19 amino acids
    (B) TYPE: amino acid
    (C) STRANDEDNESS: single
    (D) TOPOLOGY: both (ii) MOLECULE TYPE: peptide (xi) SEQUENCE DESCRIPTION: SEQ ID NO:41:

Leu Ser Ala Glu Ile Asn Arg Pro Asp Tyr Leu Asp Phe Ala Glu
1               5                   10                  15

Ser Gly Gln Val ( 2 ) INFORMATION FOR SEQ ID NO:42:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: both ( i i ) MOLECULE TYPE: peptide ( x i ) SEQUENCE DESCRIPTION: SEQ ID NO:42:

```
Val Ala His Val Val Ala Asn Pro Gln Ala Glu Gly Gln Leu
 1               5                  10
```

( 2 ) INFORMATION FOR SEQ ID NO:43:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: both ( i i ) MOLECULE TYPE: peptide ( x i ) SEQUENCE DESCRIPTION: SEQ ID NO:43:

```
Ala Glu Gly Gln Leu Gln Trp Leu Asn Arg Arg Ala Asn Ala Leu
 1               5                  10                  15
Leu Ala Asn Gly
```

( 2 ) INFORMATION FOR SEQ ID NO:44:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: both ( i i ) MOLECULE TYPE: peptide ( x i ) SEQUENCE DESCRIPTION: SEQ ID NO:44:

```
Gly Leu Tyr Leu Ile Tyr Ser Gln Val Leu Phe Lys Gly Gln Gly
 1               5                  10                  15
```

( 2 ) INFORMATION FOR SEQ ID NO:45:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: both ( i i ) MOLECULE TYPE: peptide ( x i ) SEQUENCE DESCRIPTION: SEQ ID NO:45:

```
His Val Leu Leu Thr His Thr Ile Ser Arg Ile Ala Val Ser Tyr
 1               5                  10                  15
Gln Thr Lys Val Asn Leu Leu
                 20
```

( 2 ) INFORMATION FOR SEQ ID NO:46:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: both ( i i ) MOLECULE TYPE: peptide (x i) SEQUENCE DESCRIPTION: SEQ ID NO:46:

Thr Ile Ser Arg Ile Ala Val Ser Tyr Gln Thr
1               5                   10

(2) INFORMATION FOR SEQ ID NO:47:

(i) SEQUENCE CHARACTERISTICS:
  (A) LENGTH: 26 amino acids
  (B) TYPE: amino acid
  (C) STRANDEDNESS: single
  (D) TOPOLOGY: both (ii) MOLECULE TYPE: peptide (x i) SEQUENCE DESCRIPTION: SEQ ID NO:47:

Leu Ser Ala Glu Ile Asn Arg Pro Asp Tyr Leu Asp Phe Ala Glu
1               5                   10                  15

Ser Gly Gln Val Tyr Phe Gly Ile Ile Ala Leu
                20              25